(12) United States Patent
Lipkens et al.

(10) Patent No.: US 9,950,282 B2
(45) Date of Patent: Apr. 24, 2018

(54) ELECTRONIC CONFIGURATION AND CONTROL FOR ACOUSTIC STANDING WAVE GENERATION

(71) Applicant: FloDesign Sonics, Inc., Wilbraham, MA (US)

(72) Inventors: Bart Lipkens, Hampden, MA (US); Ronald Musiak, Westfield, MA (US); Dane Mealey, Springfield, MA (US); Ali Shajii, Weston, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

(21) Appl. No.: 15/495,471

(22) Filed: Apr. 24, 2017

(65) Prior Publication Data
US 2017/0291122 A1     Oct. 12, 2017

Related U.S. Application Data

(63) Continuation-in-part of application No. 15/371,037, filed on Dec. 6, 2016, which is a continuation of
(Continued)

(51) Int. Cl.
    *C02F 1/36*      (2006.01)
    *B01D 17/12*     (2006.01)
    (Continued)

(52) U.S. Cl.
    CPC ......... *B01D 17/12* (2013.01); *A61M 1/3678* (2014.02); *B01D 17/06* (2013.01);
    (Continued)

(58) Field of Classification Search
    CPC .......... B01D 21/283; B01D 2021/0081; B01D 43/00; B01D 21/28; B01J 19/10;
    (Continued)

(56) References Cited

U.S. PATENT DOCUMENTS 2,473,971 A    6/1949  Ross
2,667,944 A    2/1954  Crites
(Continued)

FOREIGN PATENT DOCUMENTS

DE    3027433     2/1982
EP    0292470     11/1988
(Continued)

OTHER PUBLICATIONS

Alvarez et al.; Shock Waves, vol. 17, No. 6, pp. 441-447, 2008.
(Continued)

*Primary Examiner* — Walter D. Griffin
*Assistant Examiner* — Cameron J Allen
(74) *Attorney, Agent, or Firm* — Patrick O'Shea, Esq.; O'Shea Getz P.C.

(57) ABSTRACT

Aspects of the disclosure are directed to an apparatus for separating a second fluid or a particulate from a host fluid. That apparatus comprises a flow chamber with at least one inlet and at least one outlet. A drive circuit configured to provide a drive signal to a filter circuit configured to receive the drive signal and provide a translated drive signal. An ultrasonic transducer is cooperatively arranged with the flow chamber, and transducer includes at least one piezoelectric element configured to be driven by the current drive signal to create an acoustic standing wave in the flow chamber. At least one reflector opposing the ultrasonic transducer to reflect acoustic energy.

17 Claims, 35 Drawing Sheets

Related U.S. Application Data application No. 14/533,753, filed on Nov. 5, 2014, now Pat. No. 9,512,395, application No. 15/495,471, which is a continuation-in-part of application No. 15/285,349, filed on Oct. 4, 2016, which is a continuation-in-part of application No. 14/708,035, filed on May 8, 2015, now Pat. No. 9,457,302, said application No. 15/285,349 is a continuation-in-part of application No. 14/026,413, filed on Sep. 13, 2013, now Pat. No. 9,458,450, which is a continuation-in-part of application No. 13/844,754, filed on Mar. 15, 2013, application No. 15/495,471, which is a continuation-in-part of application No. 15/284,529, filed on Oct. 3, 2016, now Pat. No. 9,796,956, and a continuation-in-part of application No. 14/533,753, filed on Nov. 5, 2014, now Pat. No. 9,512,395.

(60) Provisional application No. 62/461,691, filed on Feb. 21, 2017, provisional application No. 62/446,356, filed on Jan. 13, 2017, provisional application No. 62/326,766, filed on Apr. 24, 2016, provisional application No. 62/020,088, filed on Jul. 2, 2014, provisional application No. 61/900,395, filed on Nov. 5, 2013, provisional application No. 61/990,168, filed on May 8, 2014, provisional application No. 61/754,792, filed on Jan. 21, 2013, provisional application No. 61/708,641, filed on Oct. 2, 2012, provisional application No. 61/611,240, filed on Mar. 15, 2012, provisional application No. 61/611,159, filed on Mar. 15, 2012, provisional application No. 62/322,262, filed on Apr. 14, 2016, provisional application No. 62/307,489, filed on Mar. 12, 2016, provisional application No. 62/235,614, filed on Oct. 1, 2015, provisional application No. 62/020,088, filed on Jul. 2, 2014, provisional application No. 61/900,635, filed on Nov. 6, 2013.

(51) Int. Cl.
*B01D 17/06* (2006.01)
*B01D 21/28* (2006.01)
*B01D 29/72* (2006.01)
*H04R 1/06* (2006.01)
*H01L 41/09* (2006.01)
*H03H 3/02* (2006.01)
*H03H 9/00* (2006.01)
*B01D 21/00* (2006.01)
*B06B 1/06* (2006.01)
*C12M 1/26* (2006.01)
*C12M 1/00* (2006.01)
*A61M 1/36* (2006.01)

(52) U.S. Cl.
CPC ......... *B01D 21/0045* (2013.01); *B01D 21/28* (2013.01); *B01D 21/283* (2013.01); *B01D 29/72* (2013.01); *B06B 1/06* (2013.01); *C02F 1/36* (2013.01); *C12M 33/08* (2013.01); *C12M 47/02* (2013.01); *H01L 41/09* (2013.01); *H03H 3/02* (2013.01); *H03H 9/009* (2013.01); *H04R 1/06* (2013.01)

(58) Field of Classification Search
CPC ..... C02F 1/36; A61L 33/0094; A61M 1/3692; A61M 1/0209; A61M 1/0281; A61M 1/3678; A61M 1/3693; F04C 2/00; B01L 3/502761; G01N 15/1459; C12N 13/00; A61K 35/18
See application file for complete search history.

(56) References Cited

U.S. PATENT DOCUMENTS

| | | |
|---|---|---|
| 3,555,311 A | 1/1971 | Weber |
| 4,055,491 A | 10/1977 | Porath-Furedi |
| 4,118,649 A | 10/1978 | Schwartzman et al. |
| 4,125,789 A * | 11/1978 | Van Schoiack .......... G01D 3/06 327/541 |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,398,325 A | 8/1983 | Piaget et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,983,189 A | 1/1991 | Peterson et al. |
| 5,085,783 A | 2/1992 | Feke et al. |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,902,489 A | 5/1999 | Yasuda et al. |
| 5,912,182 A | 6/1999 | Coakley et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,332,541 B1 | 12/2001 | Coakley et al. |
| 6,391,653 B1 | 5/2002 | Letcher et al. |
| 6,487,095 B1 | 11/2002 | Malik et al. |
| 6,592,821 B1 | 7/2003 | Wada et al. |
| 6,649,069 B2 | 11/2003 | DeAngelis |
| 6,699,711 B1 | 3/2004 | Hahn et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |

(56) References Cited

U.S. PATENT DOCUMENTS

| | | | |
|---|---|---|---|
| 8,679,338 | B2 | 3/2014 | Rietman et al. |
| 8,714,360 | B2 | 5/2014 | Swayze et al. |
| 2002/0038662 | A1 | 4/2002 | Schuler et al. |
| 2002/0134734 | A1 | 9/2002 | Campbell et al. |
| 2003/0195496 | A1 | 10/2003 | Maguire |
| 2003/0209500 | A1 | 11/2003 | Kock et al. |
| 2003/0230535 | A1 | 12/2003 | Affeld et al. |
| 2004/0016699 | A1 | 1/2004 | Bayevsky |
| 2005/0031499 | A1 | 2/2005 | Meier |
| 2005/0145567 | A1* | 7/2005 | Quintel ............... B01D 29/115 210/636 |
| 2005/0150830 | A1 | 7/2005 | Laugham |
| 2005/0196725 | A1 | 9/2005 | Fu |
| 2006/0037915 | A1 | 2/2006 | Strand et al. |
| 2007/0272618 | A1 | 11/2007 | Gou et al. |
| 2007/0284299 | A1 | 12/2007 | Xu et al. |
| 2008/0105625 | A1 | 5/2008 | Rosenberg |
| 2008/0217259 | A1 | 9/2008 | Siversson |
| 2009/0029870 | A1 | 1/2009 | Ward et al. |
| 2009/0045107 | A1 | 2/2009 | Ward et al. |
| 2009/0053686 | A1 | 2/2009 | Ward et al. |
| 2009/0098027 | A1 | 4/2009 | Tabata et al. |
| 2009/0178716 | A1 | 7/2009 | Kaduchak et al. |
| 2009/0194420 | A1 | 8/2009 | Mariella, Jr. et al. |
| 2009/0226994 | A1 | 9/2009 | Lemor et al. |
| 2009/0227042 | A1 | 9/2009 | Gauer |
| 2009/0295505 | A1 | 12/2009 | Mohammadi et al. |
| 2010/0000945 | A1 | 1/2010 | Gavalas |
| 2010/0078384 | A1 | 4/2010 | Yang |
| 2010/0124142 | A1 | 5/2010 | Laugham et al. |
| 2010/0192693 | A1 | 8/2010 | Mudge et al. |
| 2010/0193407 | A1 | 8/2010 | Steinberg et al. |
| 2010/0206818 | A1* | 8/2010 | Leong ............... B01D 21/283 210/748.05 |
| 2010/0255573 | A1 | 10/2010 | Bond et al. |
| 2010/0261918 | A1 | 10/2010 | Chianelli et al. |
| 2010/0317088 | A1 | 12/2010 | Radaelli et al. |
| 2010/0323342 | A1 | 12/2010 | Gonzalez Gomez et al. |
| 2010/0330633 | A1 | 12/2010 | Walther et al. |
| 2011/0003350 | A1 | 1/2011 | Schafran et al. |
| 2011/0024335 | A1 | 2/2011 | Ward et al. |
| 2011/0092726 | A1 | 4/2011 | Clarke |
| 2011/0095225 | A1 | 4/2011 | Eckelberry et al. |
| 2011/0123392 | A1 | 5/2011 | Dionne et al. |
| 2011/0154890 | A1 | 6/2011 | Holm et al. |
| 2011/0166551 | A1 | 7/2011 | Schafer |
| 2011/0262990 | A1 | 10/2011 | Wang et al. |
| 2011/0278218 | A1 | 11/2011 | Dionne et al. |
| 2011/0281319 | A1 | 11/2011 | Swayze et al. |
| 2011/0309020 | A1 | 12/2011 | Rietman et al. |
| 2012/0088295 | A1 | 4/2012 | Yasuda et al. |
| 2012/0161903 | A1* | 6/2012 | Thomas ............... H03H 9/6433 333/195 |
| 2012/0163126 | A1 | 6/2012 | Campbell et al. |
| 2012/0328477 | A1 | 12/2012 | Dionne |
| 2012/0329122 | A1 | 12/2012 | Lipkens et al. |
| 2013/0175226 | A1 | 7/2013 | Coussios |
| 2013/0277316 | A1 | 10/2013 | Dutra et al. |
| 2013/0284271 | A1 | 10/2013 | Lipkens et al. |
| 2014/0011240 | A1 | 1/2014 | Lipkens et al. |
| 2014/0377834 | A1 | 12/2014 | Presz, Jr. et al. |

FOREIGN PATENT DOCUMENTS

| | | |
|---|---|---|
| EP | 1254669 | 11/2002 |
| GB | 2420510 | 5/2006 |
| WO | 198707178 | 12/1987 |
| WO | 0041794 | 7/2000 |
| WO | 02072234 | 9/2002 |
| WO | 2009111276 | 9/2009 |
| WO | 2009144709 | 12/2009 |
| WO | 2010024753 | 4/2010 |
| WO | 2011023949 | 3/2011 |
| WO | 2011027146 | 3/2011 |
| WO | 2011161463 | 12/2011 |
| WO | WO2015154999 A1 | 10/2015 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10 .1038/N NANO .2009 .177.

Seymour et al, J. Chem. Edu., 1990, 67(9), p. 763, published Sep. 1990.

Phys. Org. "Engineers develop revolutionary nanotech water desalination membrane." Nov. 6, 2006. http://phys.org/news82047372.html.

"Proceedings of the Acoustics 2012 Nantes Conference," Apr. 23-27, 2012, Nantes, France, pp. 278-282.

Sony New Release: <http://www.sony.net/SonyInfo/News/Press/201010/10-37E/index.html>.

Lipkens et al. "The Effect of Frequency Sweeping and Fluid Flow on Particle Trajectories in Ultrasonic Standing Waves", IEEE Sensors Journal, vol. 8, No. 6, Jun. 1, 2008, pp. 667-677.

International Search Report for PCT/US2017/029145 dated Jul. 20, 2017.

Wang et al. "Retention and Viability Characteristics of Mammalian Cells in an Acoustically Driven Polymer Mesh", Biotechnol Prog.

(56) References Cited

OTHER PUBLICATIONS

Jan.-Feb. 2004; 20(1):384-7; p. 384, col. 1, para 2, para 1; Fig 1; p. 385, col. 2, para 2; p. 385, col. 1, para 1; p. 385, col. 1, para 2; p. 384, para 3; p. 384; col. 2, ast para; p. 385, col. 1 para 1.

* cited by examiner

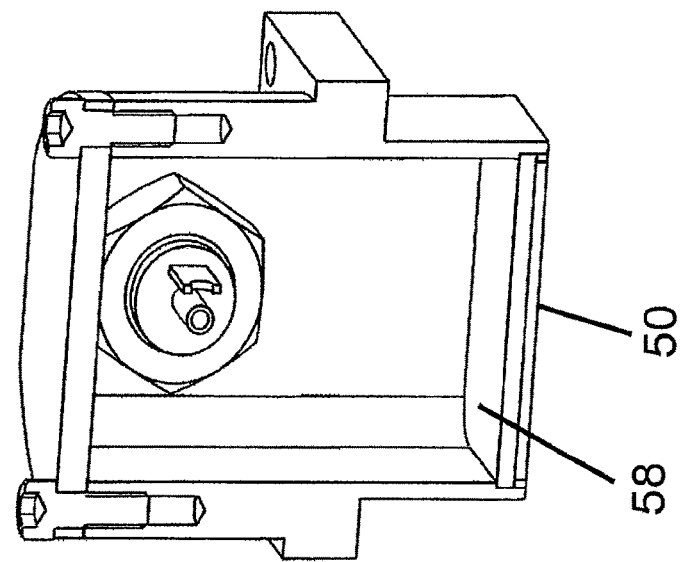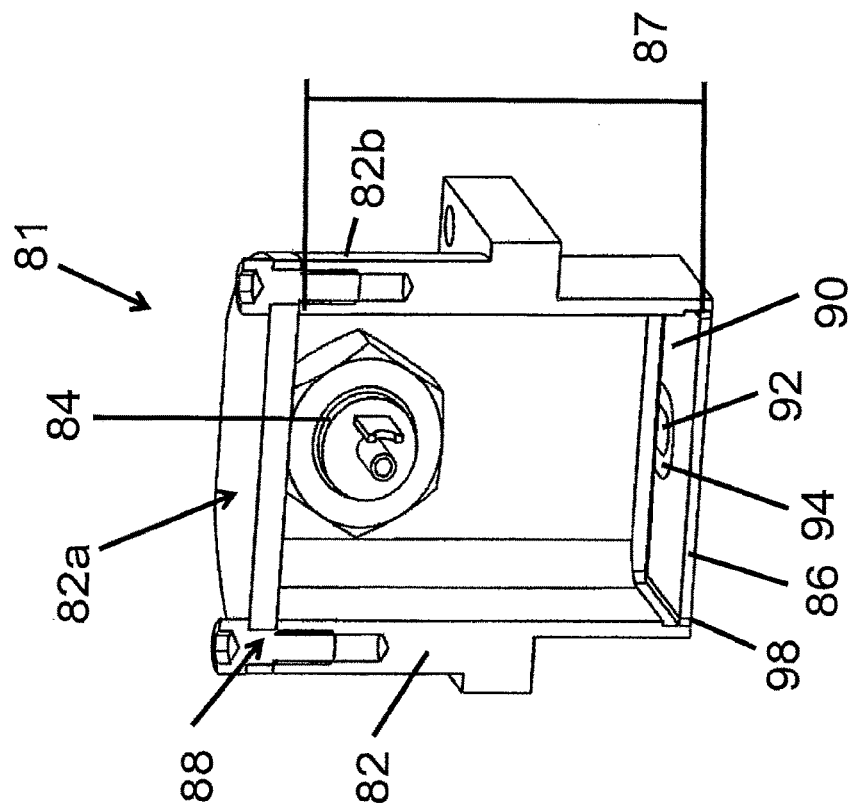

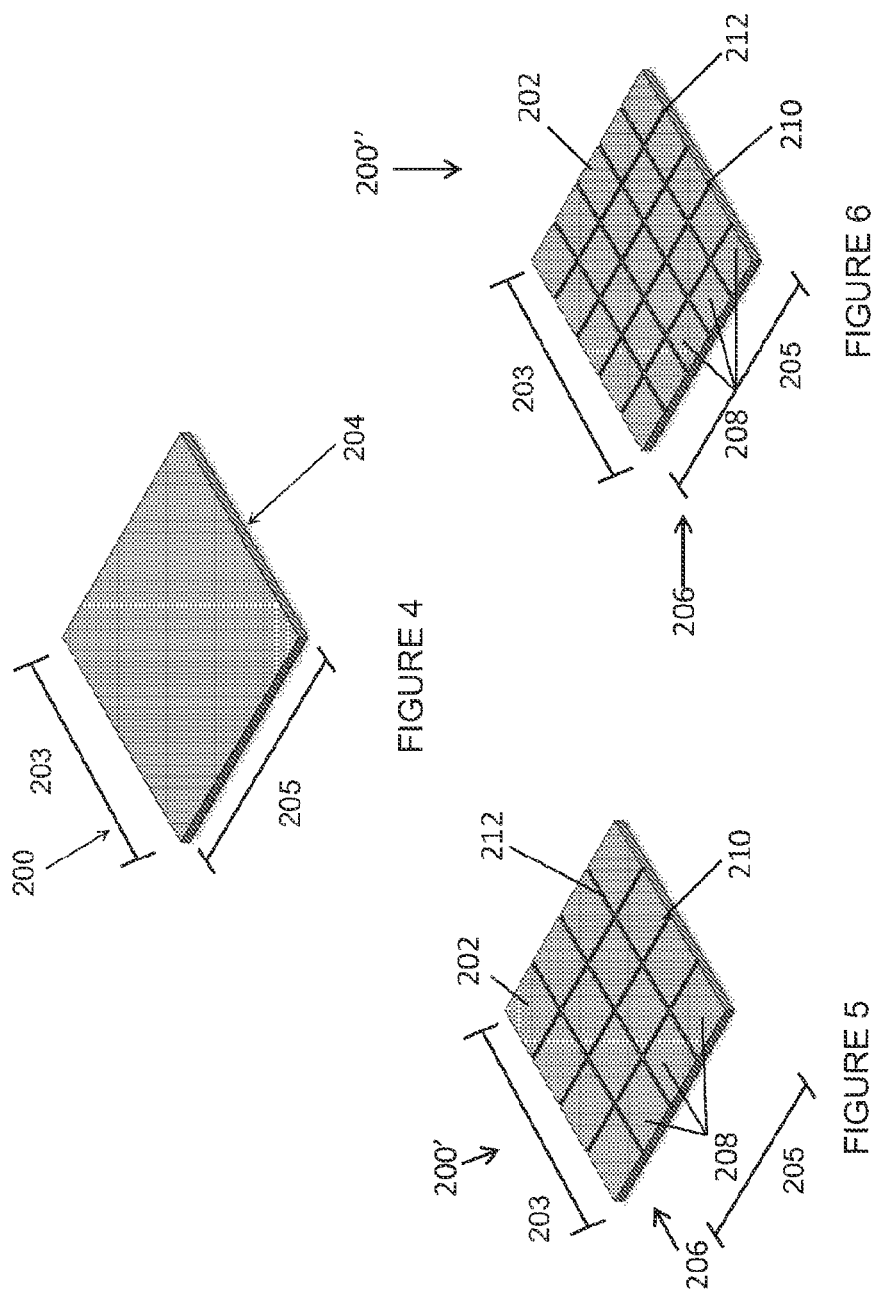

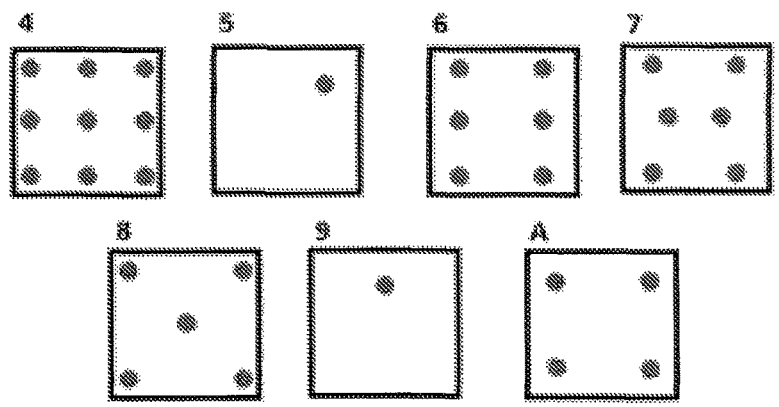
FIG. 9A
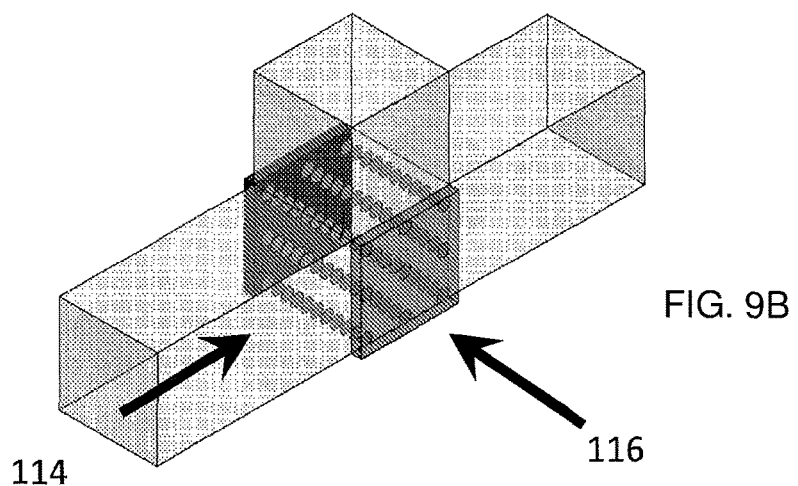
FIG. 9B
114   116
FIG. 9C
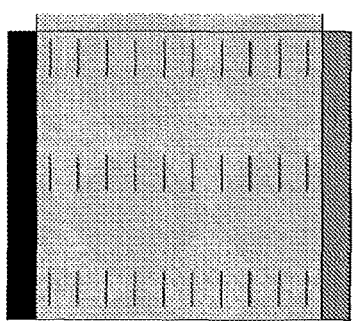
FIG. 9D
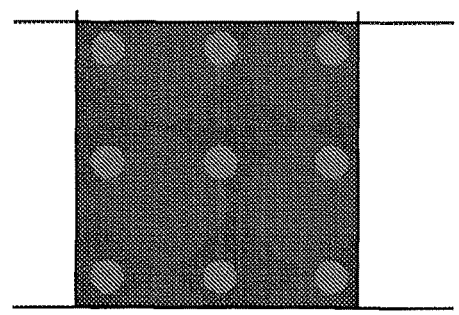

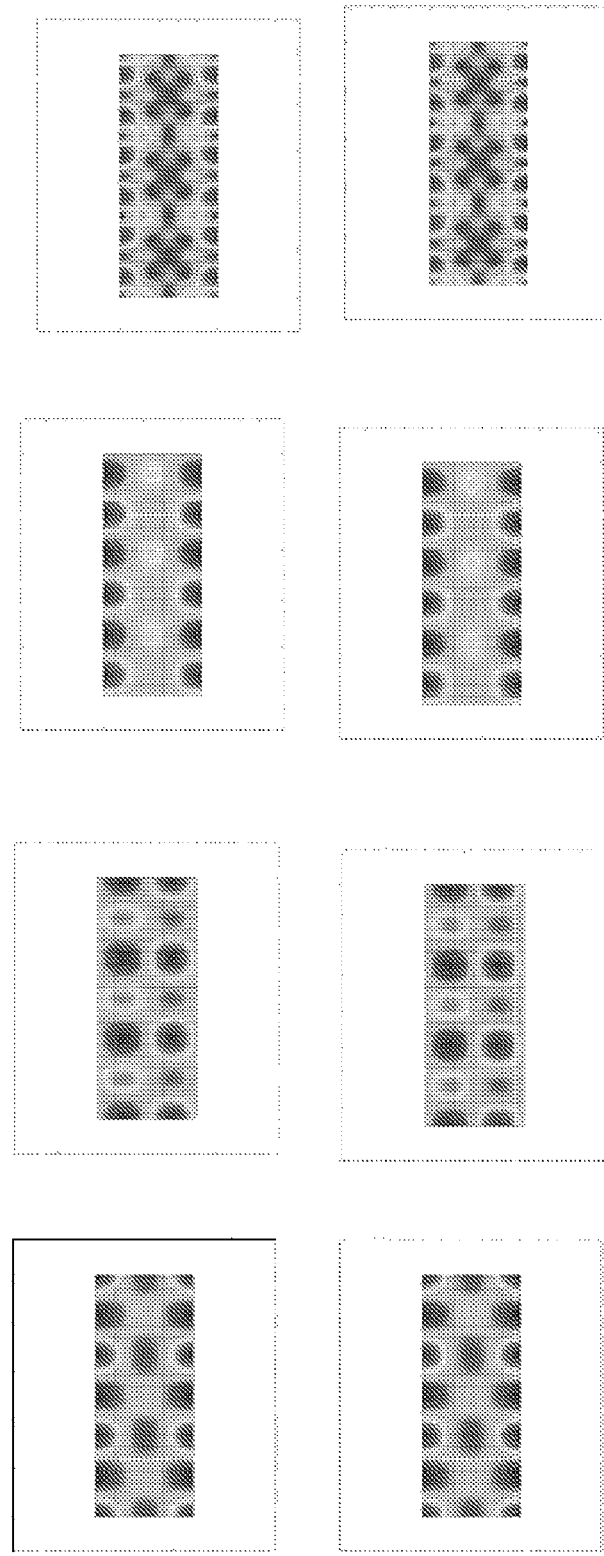

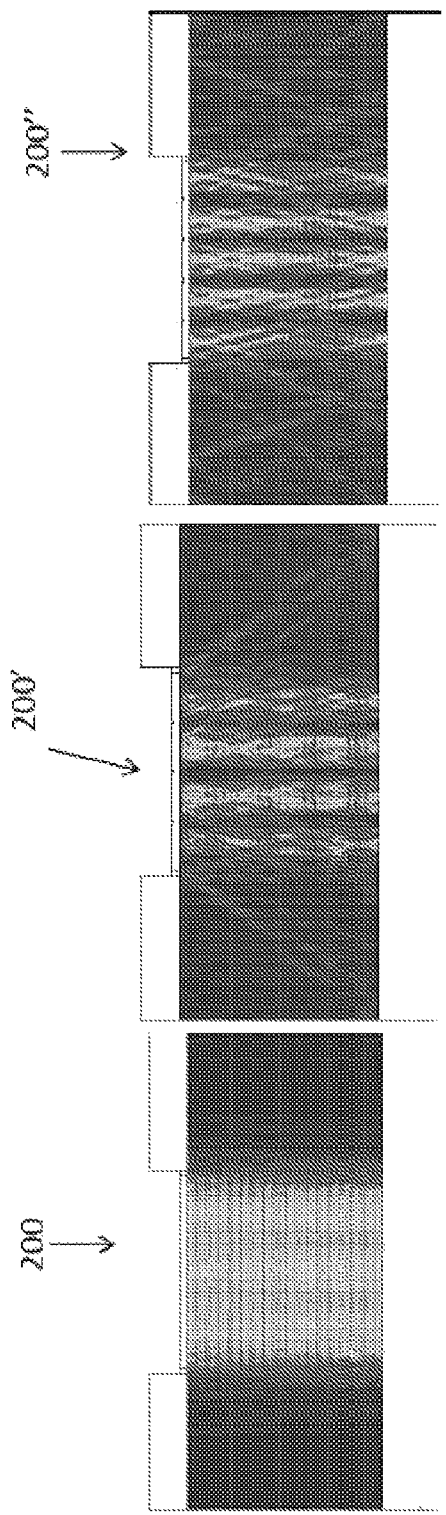

- Use of current source to drive the crystal
  - Enhanced performance for the specific application
- Use of VI-sensing to control the frequency and delivered power:
  - Optimize performance
  - Detect Degradation

ELECTRONIC CONFIGURATION AND CONTROL FOR ACOUSTIC STANDING WAVE GENERATION

CROSS REFERENCE TO RELATED APPLICATIONS

This application claims the benefit of U.S. Provisional Patent Application Ser. No. 62/461,691 (P-095) filed Feb. 21, 2017, U.S. Provisional Patent Application Ser. No. 62/446,356 (P-094) filed Jan. 13, 2017, and U.S. Provisional Patent Application Ser. No. 62/326,766 (P-065) filed Apr. 24, 2016, and this application is a continuation-in-part of U.S. patent application Ser. No. 15/371,037 filed Dec. 12, 2016, which is a continuation of U.S. Pat. No. 9,512,395 filed Nov. 5, 2014, which claims priority to U.S. Provisional Patent Application Ser. No. 62/020,088 filed Jul. 2, 2014 and U.S. Provisional Patent Application Ser. No. 61/900,395 filed Nov. 5, 2013, a continuation-in-part of U.S. patent application Ser. No. 15/285,349 filed Oct. 4, 2016, which is a continuation-in-part of U.S. Pat. No. 9,457,302 filed May 8, 2015, which claims priority to U.S. Provisional Patent Application Ser. No. 61/990,168, and is a continuation-in-part of U.S. patent application Ser. No. 14/026,413 filed Sep. 13, 2013, which is a continuation-in-part of U.S. patent application Ser. No. 13/844,754 filed Mar. 15, 2013, which claims priority to U.S. Provisional Patent Application Ser. No. 61/754,792 filed Jan. 21, 2013, U.S. Provisional Patent Application Ser. No. 61/708,641 filed Oct. 2, 2012, U.S. Provisional Patent Application Ser. No. 61/611,240 filed Mar. 15, 2012 and U.S. Provisional Patent Application Ser. No. 61/611,159 filed Mar. 15, 2012, and is a continuation-in-part of U.S. patent application Ser. No. 15/284,529 filed Oct. 3, 2016, which claims priority to U.S. Provisional Application Ser. No. 62/322,262 filed Apr. 14, 2016, U.S. Provisional Application Ser. No. 62/307,489 filed Mar. 12, 2016, and U.S. Provisional Application Ser. No. 62/235,614 filed Oct. 1, 2015, and is a continuation-in-part of U.S. Pat. No. 9,512,395 filed Nov. 5, 2014, which claims priority to U.S. Provisional Patent Application Ser. No. 62/020,088 filed Jul. 2, 2014 and U.S. Provisional Patent Application Ser. No. 61/900,635 filed Nov. 6, 2013. These applications are incorporated herein by reference in their entireties.

BACKGROUND

Acoustophoresis is the separation of particles and secondary fluids from a primary or host fluid using acoustics, such as acoustic standing waves. Acoustic standing waves can exert forces on particles in a fluid when there is a differential in density and/or compressibility, otherwise known as the acoustic contrast factor. The pressure profile in a standing wave contains areas of local minimum pressure amplitudes at standing wave nodes and local maxima at standing wave anti-nodes. Depending on their density and compressibility, the particles can be trapped at the nodes or anti-nodes of the standing wave. Generally, the higher the frequency of the standing wave, the smaller the particles that can be trapped.

At a micro scale, for example with structure dimensions on the order of micrometers, conventional acoustophoresis systems tend to use half or quarter wavelength acoustic chambers, which at frequencies of a few megahertz are typically less than a millimeter in thickness, and operate at very slow flow rates (e.g., µL/min). Such systems are not scalable since they benefit from extremely low Reynolds number, laminar flow operation, and minimal fluid dynamic optimization.

At the macro-scale, planar acoustic standing waves have been used in separation processes. However, a single planar wave tends to trap the particles or secondary fluid such that separation from the primary fluid is achieved by turning off or removing the planar standing wave. The removal of the planar standing wave may hinder continuous operation. Also, the amount of power that is used to generate the acoustic planar standing wave tends to heat the primary fluid through waste energy, which may be disadvantageous for the material being processed.

Conventional acoustophoresis devices have thus had limited efficacy due to several factors including heat generation, use of planar standing waves, limits on fluid flow, and the inability to capture different types of materials.

Control of power supplied to an ultrasonic transducer is challenging to implement, and in particular is challenging to implement with efficient performance. Promoting multimode behavior in a resonance-cavity system may depend on providing sufficient electrical power to an ultrasonic transducer in the system.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Examples of the disclosure are directed to an apparatus for separating a second fluid or a particulate from a host fluid, comprising a flow chamber having opposing first and second walls, at least one inlet and at least one outlet. A control circuit provides a drive signal and a scaling circuit receives the drive signal and provides an equivalent current source drive signal, where the scaling circuit provides impedance and source translation with respect to the ultrasonic transducer. An ultrasonic transducer, having a transducer input impedance and located within the flow chamber includes at least one piezoelectric element driven by the equivalent current source drive signal to create an acoustic standing wave in the flow chamber. At least one reflector is located on the first wall on the opposite side of the flow chamber from the at least one ultrasonic transducer.

The control circuit may comprise a voltage source.

The acoustic standing wave may comprise a multi-dimensional acoustic standing wave. The multi-dimensional acoustic standing wave may be generated from a single piezoelectric element or a plurality of piezoelectric elements, perturbed in a higher order mode.

The scaling circuit may comprise an inductor that includes a first terminal and a second terminal, and a capacitor that includes a third terminal and a fourth terminal, where the first terminal receives the drive signal, the second and third terminals are connected, the fourth terminal is connected to a reference potential, and a signal indicative of the equivalent current source drive signal is provided at the second and third terminals.

The scaling circuit may consist of passive circuit components.

Aspects of the disclosure are also directed to an apparatus for separating a secondary fluid or particulates from a host fluid, comprising a flow chamber having opposing first and second walls, at least one inlet and at least one outlet. A circuit is configured to receive a drive signal and provides a translated drive signal. An ultrasonic transducer is located within the flow chamber, the transducer includes at least one piezoelectric element that receive the translated drive signal to create an acoustic standing wave in the flow chamber. At least one reflector is located on the wall on the opposite side of the flow chamber from the at least one ultrasonic transducer.

The acoustic standing wave may include a multi-dimensional acoustic standing wave.

The circuit may comprise a scaling circuit that receives the drive signal and provides the translated drive signal, where the scaling circuit provides impedance and source translation with respect to the ultrasonic transducer.

The scaling circuit may comprise a first inductor, a first capacitor and a second inductor cooperatively arranged as a low pass filter.

The scaling circuit may comprise an inductor that includes a first terminal and a second terminal, and a capacitor that includes a third terminal and a fourth terminal, where the first terminal receives the drive signal, the second and third terminals are connected, the fourth terminal is connected to a reference potential, and a signal indicative of the equivalent translated drive signal is provided at the second and third terminals.

The scaling circuit may consist of passive circuit components.

A first tap may sense voltage across the ultrasonic transducer. The transducer may be composed of or include piezoelectric material, which may be implemented as a ceramic crystal, a poly-crystal or other crystal, all of which may collectively be referred to herein as a crystal. The first tap may provide a sensed voltage signal indicative of a voltage across the transducer, and a current sensing coil may sense current and provide a sensed current signal indicative of crystal current.

A controller may receive and process the sensed current signal and the sensed voltage signal to control the drive signal.

The circuit may comprise a first inductor that includes a first terminal and a second terminal, a first capacitor that includes a third terminal and a fourth terminal, and a second inductor that includes a fifth terminal and sixth terminal, there the first terminal receives a signal indicative of the drive signal, the second terminal is connected to the third terminal and the fifth terminal, the fourth terminal is connected to a reference voltage, and an output signal indicative of the current drive signal is provided on the sixth terminal.

Aspects of the disclosure are further directed to an apparatus for separating a second fluid or a particulate from a host fluid, comprising a flow chamber having opposing first and second walls, and at least one inlet and at least one outlet. A drive circuit is configured to provide a drive signal, and a filter circuit is configured to receive the drive signal and provide a translated drive signal. An ultrasonic transducer is cooperatively arranged with the flow chamber, the transducer including one or more at least one piezoelectric element driven by the current drive signal to create an acoustic standing wave in the flow chamber. At least one reflector is located on the second wall opposing the ultrasonic transducer to receive the acoustic standing waves.

The acoustic standing wave may comprise a multi-dimensional acoustic standing wave.

The filter circuit may comprise an inductor that includes a first terminal and a second terminal, and a capacitor that includes a third terminal and a fourth terminal, where the first terminal receives the drive signal, the second and third terminals are connected, the fourth terminal is connected to a reference potential, and a signal indicative of the equivalent current source drive signal is provided at the second and third terminals.

The filter circuit may comprise a first inductor that includes a first terminal and a second terminal, a first capacitor that includes a third terminal and a fourth terminal, and a second inductor that includes a fifth terminal and sixth terminal, there the first terminal receives a signal indicative of the drive signal, the second terminal is connected to the third terminal and the fifth terminal, the fourth terminal is connected to a reference voltage, and an output signal indicative of the current drive signal is provided on the sixth terminal.

The filter may consist of passive circuit components.

The voltage drive signal may be substantially a square wave, and the translated signal may be substantially a sine wave.

BRIEF DESCRIPTION OF THE DRAWINGS

The following is a brief description of the drawings, which are presented for the purposes of illustrating the exemplary embodiments disclosed herein and not for the purposes of limiting the same.

FIG. 3A is a cross-sectional diagram of an ultrasonic transducer structure that can be used in the present disclosure. An air gap is present within the transducer, and no backing layer or wear plate is present.

FIG. 3B is a cross-sectional diagram of an ultrasonic transducer structure that can be used in the present disclosure. An air gap is present within the transducer, and a backing layer and wear plate are present.

FIG. 4 is a conventional single-piece monolithic piezoelectric crystal used in an ultrasonic transducer.

FIG. 5 is an exemplary rectangular piezoelectric array having 16 piezoelectric elements used in the transducers of the present disclosure.

FIG. 6 is another exemplary rectangular piezoelectric array having 25 piezoelectric elements used in the transducers of the present disclosure.

FIG. 9A illustrates the trapping line configurations for seven of the minima amplitudes of FIG. 8 from the direction orthogonal to fluid flow.

FIG. 9B is a perspective view illustrating the separator. The fluid flow direction and the trapping lines are shown.

FIG. 9C is a view from the fluid inlet along the fluid flow direction (arrow 114) of FIG. 9B, showing the trapping nodes of the standing wave where particles would be captured.

FIG. 9D is a view taken through the transducers face at the trapping line configurations, along arrow 116 as shown in FIG. 9B.

FIGS. 14A-14D are diagrams comparing the results of the numerical model (bottom) of FIG. 13 against published data (top), illustrating the accuracy of the numerical model. FIG. 14A compares the acoustic potential U. FIG. 14B compares the x-component of the acoustic radiation force (ARF). FIG. 14C compares the y-component of the ARF. FIG. 14D compares the absolute value of the ARF.

FIG. 15 is a diagram showing the amplitude of the acoustic standing wave generated by a monolithic piezoelectric crystal in the model of FIG. 13. The frequency is at 2.245 MHz. The horizontal axis is the location along the X-axis, and the vertical axis is the location along the Y-axis between the transducer and the reflector.

FIG. 16 is a diagram showing the amplitude of the acoustic standing wave generated by the 4-element piezoelectric array in the model of FIG. 13. The frequency is at 2.245 MHz with phasing between the elements being varied.

FIG. 17 is a diagram showing the amplitude of the acoustic standing wave generated by the 5-element piezoelectric array in the model of FIG. 13. The frequency is at 2.245 MHz with phasing between the elements being varied.

DETAILED DESCRIPTION

Figure 1A:
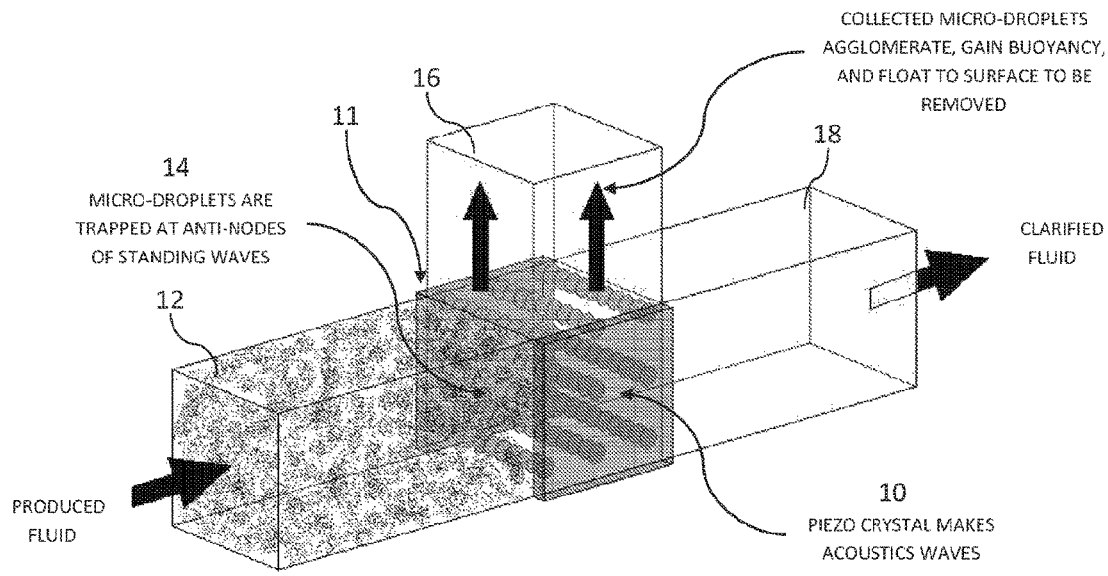
FIG. 1A is a diagram illustrating the function of an acoustophoretic separator with a secondary fluid or particles less dense than the host fluid.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

The term "comprising" is used herein as requiring the presence of the named components/steps and allowing the presence of other components/steps. The term "comprising" should be construed to include the term "consisting of", which allows the presence of only the named components/ steps, along with any impurities that might result from the manufacture of the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "substantially" and "about" can be used to include any numerical value that can vary without changing the basic function of that value. When used with a range, "substantially" and "about" also disclose the range defined by the absolute values of the two endpoints, e.g. "about 2 to about 4" also discloses the range "from 2 to 4." The terms "substantially" and "about" may refer to plus or minus 10% of the indicated number.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. The terms "above" and "below", or "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value less than 10.

The acoustophoretic separation technology of the present disclosure employs ultrasonic acoustic standing waves to trap, i.e., hold stationary, particles or a secondary fluid in a host fluid stream. The particles or secondary fluid collect at the nodes or anti-nodes of the multi-dimensional acoustic standing wave, depending on the particles' or secondary fluid's acoustic contrast factor relative to the host fluid, forming clusters that eventually fall out of the multi-dimensional acoustic standing wave when the clusters have grown to a size large enough to overcome the holding force of the multi-dimensional acoustic standing wave (e.g. by coalescence or agglomeration). The scattering of the acoustic field off the particles results in a three-dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable axial positions within the standing waves. When the acoustic radiation force exerted on the particles is stronger than the combined effect of fluid drag force and buoyancy and gravitational force, the particle is trapped within the acoustic standing wave field. This continuous trapping results in concentration, aggregation, clustering, agglomeration and/or coalescence of the trapped particles that will then continuously fall out of the multi-dimensional acoustic standing wave through gravity separation. The strong lateral forces create rapid clustering of particles. Relatively large solids of one material can thus be separated from smaller particles of a different material, the same material, and/or the host fluid through enhanced gravitational separation.

In this regard, the contrast factor is the difference between the compressibility and density of the particles and the fluid itself. These properties are characteristic of the particles and the fluid themselves. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the acoustic radiation force trap the cells. The radial or lateral component of the ARF is larger than the combined effect of fluid drag force and gravitational force. The radial or lateral component drives the cells/particles to planes where they can cluster into larger groups, which will then gravity separate from the fluid.

As the cells agglomerate at the nodes of the standing wave, there is also a physical scrubbing of the cell culture media that occurs whereby more cells are trapped as they come in contact with the cells that are already held within the standing wave. This effect contributes to separating the cells from the cell culture media. The expressed biomolecules remain in the nutrient fluid stream (i.e. cell culture medium).

For three-dimensional acoustic fields, Gor'kov's formulation can be used to calculate the acoustic radiation force $F_{ac}$ applicable to any sound field. The primary acoustic radiation force $F_{ac}$ is defined as a function of a field potential U, $$F_A = -\Lambda(U),$$

where the field potential U is defined as $$U = V_0 \left[ \frac{\langle p^2 \rangle}{2\rho_f c_f^2} f_1 - \frac{3\rho_f \langle u^2 \rangle}{4} f_2 \right]$$

and $f_1$ and $f_2$ are the monopole and dipole contributions defined by $$f_1 = 1 - \frac{1}{\Lambda \sigma^2}, f_2 = \frac{2(\Lambda - 1)}{2\Lambda + 1},$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and $<>$ indicates time averaging over the period of the wave. Gor'kov's formulation applies to particles smaller than the wavelength. For larger particle sizes, Ilinskii provides equations for calculating the 3D acoustic radiation forces for any particle size. See Ilinskii, *Acoustic Radiation Force on a Sphere in Tissue*, The Journal of the Acoustical Society of America, 132, 3, 1954 (2012), which is incorporated herein by reference.

An acoustic transducer can be driven to produce an acoustic wave. The acoustic wave can be reflected with another acoustic transducer or a reflector to generate an acoustic standing wave. Alternately, or in addition, two opposing acoustic transducers can be driven to generate an acoustic standing wave between them. Perturbation of the piezoelectric crystal in an ultrasonic transducer in a multi-mode fashion allows for generation of a multidimensional acoustic standing wave. A piezoelectric material or crystal can be specifically designed to deform in a multimode fashion at designed frequencies, allowing for generation of a multi-dimensional acoustic standing wave. The multi-dimensional acoustic standing wave may be generated by distinct modes of the piezoelectric material or crystal such as the 3×3 mode that would generate multidimensional acoustic standing waves. A multitude of multidimensional acoustic standing waves may also be generated by allowing the piezoelectric material or crystal to vibrate through many different mode shapes. Thus, the crystal would excite multiple modes such as a 0×0 mode (i.e. a piston mode) to a 1×1, 2×2, 1×3, 3×1, 3×3, and the other higher order modes and then cycle back through the lower modes of the crystal (not necessarily in straight order). This switching or dithering of the piezoelectric material or crystal between modes allows for various multidimensional wave shapes, along with a single piston mode shape to be generated over a designated time.

In some examples of the present disclosure, a single ultrasonic transducer contains a rectangular array of piezoelectric elements, which can be operated such that some components of the array will be out of phase with other components of the array. This phased-array arrangement can also separate materials in a fluid stream. A single piezoelectric element may be used rather than a piezoelectric array.

One specific application for the acoustophoresis device is in the processing of bioreactor materials. In a fed batch bioreactor, it is important at the end of the production cycle to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. The use of acoustophoresis is an improvement over the current filtration processes (depth filtration, tangential flow filtration, centrifugation), which show limited efficiencies at high cell densities, so that the loss of the expressed materials in the filter beds themselves can be up to 5% of the materials produced by the bioreactor. The use of mammalian cell culture includes Chinese hamster ovary (CHO), NS0 hybridoma cells, baby hamster kidney (BHK) cells, and human cells has proven to be a very efficacious way of producing/expressing the recombinant proteins and monoclonal antibodies used to produce pharmaceuticals. The filtration of the mammalian cells and the mammalian cell debris through acoustophoresis aids in greatly increasing the yield of the fed batch bioreactor. The acoustophoresis process, through the use of multidimensional acoustic waves, may also be coupled with a standard filtration process upstream or downstream, such as depth filtration using diatomaceous earth, tangential flow filtration (TFF), or other physical filtration processes.

Another type of bioreactor, a perfusion reactor, uses continuous expression of the target protein or monoclonal antibodies from the CHO cells. The continuous nature of the perfusion reactor enables a much smaller footprint in faster production cycle. The use of acoustophoresis to hold the CHO cells in a fluid stream as they are producing/expressing the proteins is a very efficient and closed loop way of production. It also allows for an increased or maximum production efficiency of the proteins and monoclonal antibodies in that none of the materials are lost in a filter bed.

In the fed batch bioreactor process, the acoustophoresis device uses singular or multiple standing waves to trap the cells and cell debris. The cells and cell debris, having a positive contrast factor, move to the nodes (as opposed to the anti-nodes) of the standing wave. As the cells and cell debris agglomerate at the nodes of the standing wave, there is also a physical scrubbing of the fluid stream that occurs whereby more cells are trapped as they come in contact with the cells that are already held within the standing wave. When the cells in the multi-dimensional acoustic standing wave agglomerate to the extent where the mass is no longer able to be held by the acoustic wave, the aggregated cells and cell debris that have been trapped fall out of the fluid stream through gravity, and can be collected separately. This effect permits cells to be separated in a continuous process of gravitational separation.

Advanced multi-physics and multiple length scale computer models and high frequency (MHz), high-power, and high-efficiency ultrasonic drivers with embedded controls have been combined to arrive at new designs of acoustic resonators driven by an array of piezoelectric transducers, resulting in acoustophoretic separation devices that far surpass current capabilities.

Desirably, such transducers generate a multi-dimensional acoustic standing wave in the fluid that exerts a lateral force on the suspended particles/secondary fluid to accompany the axial force so as to increase the particle trapping capabilities of an acoustophoretic system. Typical results published in literature state that the lateral force is two orders of magnitude smaller than the axial force. In contrast, the technology disclosed in this application provides for a lateral force to be of the same order of magnitude as the axial force.

The system may be driven by a controller and amplifier (not shown). The system performance may be monitored and controlled by the controller. The parameters of the excitation of the transducer may be modulated. For example, the frequency, current or voltage of the transducer excitation or drive signal may be modulated to change characteristics of the generated acoustic standing wave. The amplitude modulation and/or by frequency modulation can be controlled by the computer. The duty cycle of the propagation of the standing wave may also be utilized to achieve certain results for trapping of materials. The acoustic standing wave may be turned on and/or shut off at different frequencies to achieve desired results.

The lateral force of the total acoustic radiation force (MU) generated by the ultrasonic transducers of the present disclosure is significant and is sufficient to overcome the fluid drag force at high linear velocities up to 2 cm/s and beyond. For example, linear velocities through the devices of the present disclosure can be as small or smaller than 4 cm/min for separation of cells/particles, and can be as high as 2 cm/sec for separation of oil/water phases. Flow rates can be as small or smaller than 25 mL/min, and can range as high as 40 mL/min to 1000 mL/min, or even higher. These flow rates in an acoustophoretic system are applicable for batch reactors, fed-batch bioreactors and perfusion bioreactors.

A diagrammatic representation of an embodiment for removing oil or other lighter-than-water material is shown in FIG. 1A. Excitation frequencies typically in the range from hundreds of kHz to 10s of MHz are applied by transducer 10. One or more standing waves are created between the transducer 10 and the reflector 11. Microdroplets or particles 12 are trapped in standing waves at the pressure anti-nodes 14 where they agglomerate, aggregate, clump, or coalesce, and, in the case of buoyant material, float to the surface and are discharged via an effluent outlet 16 located above the flow path. Clarified fluid is discharged at outlet 18. The acoustophoretic separation technology can accomplish multi-component particle separation without any fouling at a much-reduced cost.

Figure 1B:
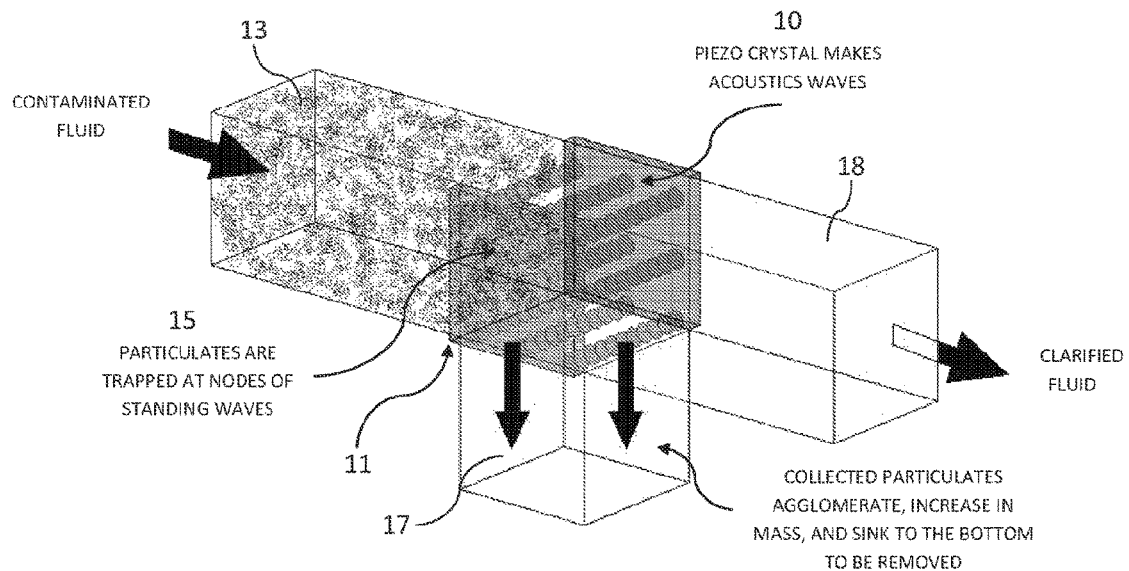
FIG. 1B is a diagram illustrating the function of an acoustophoretic separator with a secondary fluid or particles denser than the host fluid.

A diagrammatic representation of an embodiment for removing contaminants or other heavier-than-water material is shown in FIG. 1B. Excitation frequencies typically in the range from hundreds of kHz to 10s of MHz are applied by transducer 10. Contaminants in the incoming fluid 13 are trapped in standing waves at the pressure nodes 15 where they agglomerate, aggregate, clump, or coalesce, and, in the case of heavier material, sink to the bottom collector and are discharged via an effluent outlet 17 located below the flow path. Clarified water is discharged at outlet 18.

Generally, the transducers are arranged so that they cover the entire cross-section of the flow path. The acoustophoretic separation system of FIG. 1A or FIG. 1B has, in certain embodiments, a square cross section of 6.375 inches×6.375 inches which operates at flow rates of up to 5 gallons per minute (GPM), or a linear velocity of 12.5 mm/sec. The transducers 10 are PZT-8 (Lead Zirconate Titanate) transducers with a 1 inch×1 inch square cross section and a nominal 2 or 3 MHz resonance frequency. Each transducer consumes about 60 W of power for droplet trapping at a flow rate of 5 GPM. This power consumption translates in an energy cost of 0.500 kW hr/m$^3$. This low power usage is an indication of the very low cost of energy of this technology. Desirably, each transducer is powered and controlled by its own amplifier. One application for this embodiment is to shift the particle size distribution through agglomeration, aggregation, clumping or coalescing of the micron-sized oil droplets into much larger droplets.

Figure 2:
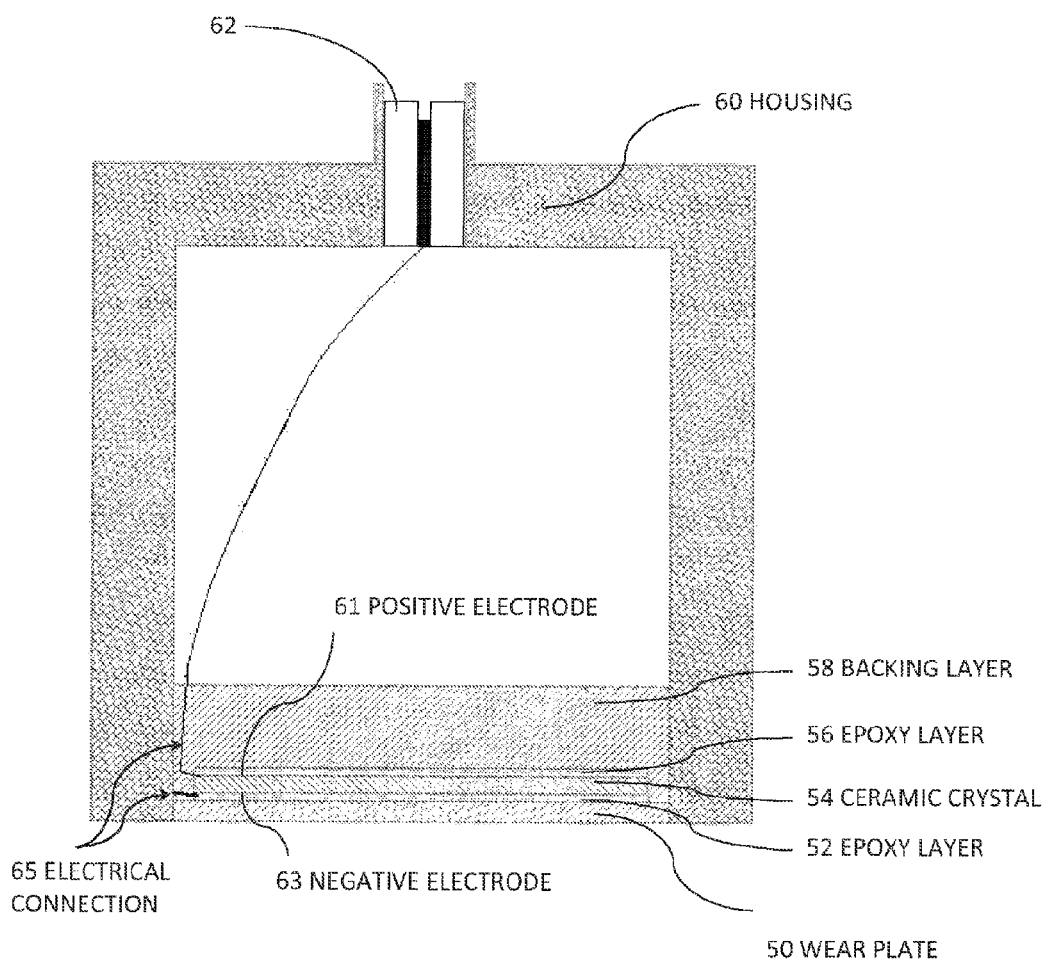
FIG. 2 is a cross-sectional diagram of a conventional ultrasonic transducer.

FIG. 2 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigenmodes. Wear plates are usually designed as impedance transformers to better match the characteristic impedance of the medium into which the transducer radiates.

FIG. 3A is a cross-sectional view of an ultrasonic transducer 81 of the present disclosure, which can be used in acoustophoretic separator. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and $O^{2-}$ ions. As an example, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer as is present in FIG. 2. Put another way, there is an air gap 87 in the transducer between aluminum top plate 82a and the crystal 86 (i.e. the air gap is completely empty). A relatively minimal backing 58 and/or wear plate 50 may be provided in some embodiments, as seen in FIG. 3B.

The transducer design can affect performance of the system. A typical transducer is a layered structure with the ceramic crystal bonded to a backing layer and a wear plate. Because the transducer is loaded with the high mechanical impedance presented by the fluid, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers have no wear plate or backing, allowing the crystal (e.g., a polycrystal, piezoelectric material or a single crystal (i.e., quartz)) to vibrate in one of its eigenmodes with a high Q-factor. The vibrating ceramic crystal/disk is directly exposed to the fluid flowing through the flow chamber.

Removing the backing (e g making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines. See the discussion below with respect to FIGS. 8-9D.

In some embodiments, the crystal may have a backing that may minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. The insertion of a layer over the PZT may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface. A glassy carbon wear layer may also be utilized. Glassy carbon, also known as vitreous carbon, is a non-graphitizing carbon which combines both glassy and ceramic properties with those of graphite. The most important properties are high temperature resistance, hardness (7 Mohs), low density, low electrical resistance, low friction and low thermal resistance. Glassy carbon also has extreme resistance to chemical attack and impermeability to gases and liquids.

In the present disclosure, the piezoelectric crystal used in each ultrasonic transducer is modified to be in the form of a segmented array of piezoelectric elements. This array is used to form a multidimensional acoustic standing wave or waves, which can be used for acoustophoresis.

FIG. 4 shows a monolithic, one-piece, single electrode piezoelectric crystal 200 that is used in ultrasonic transducers. The piezoelectric crystal has a substantially square shape, with a length 203 and a width 205 that are substantially equal to each other (e.g. about one inch). The crystal 200 has an inner surface 202, and the crystal also has an outer surface 204 on an opposite side of the crystal which is usually exposed to fluid flowing through the acoustophoretic device. The outer surface and the inner surface are relatively large in area, and the crystal is relatively thin (e.g. about 0.040 inches for a 2 MHz crystal).

FIG. 5 shows a piezoelectric crystal 200' of the present disclosure. The inner surface 202 of this piezoelectric crystal 200' is divided into a piezoelectric array 206 with a plurality of (i.e. at least two) piezoelectric elements 208. However, the array is still a single crystal. The piezoelectric elements 208 are separated from each other by one or more channels or kerfs 210 in the inner surface 202. The width of the channel (i.e. between piezoelectric elements) may be on the order of from about 0.001 inches to about 0.02 inches. The depth of the channel can be from about 0.001 inches to about 0.02 inches. In some instances, a potting material 212 (i.e., epoxy, Sil-Gel, and the like) can be inserted into the channels 210 between the piezoelectric elements. The potting material 212 is non-conducting, acts as an insulator between adjacent piezoelectric elements 208, and also acts to hold the separate piezoelectric elements 208 together. Here, the array 206 contains sixteen piezoelectric elements 208 (although any number of piezoelectric elements is possible), arranged in a rectangular 4×4 configuration (square is a subset of rectangular). Each of the piezoelectric elements 208 has substantially the same dimensions as each other. The overall array 200' has the same length 203 and width 205 as the single crystal illustrated in FIG. 4.

FIG. 6 shows another embodiment of a transducer 200". The transducer 200" is substantially similar to the transducer 200" of FIG. 5, except that the array 206 is formed from twenty-five piezoelectric elements 208 in a 5×5 configuration. Again, the overall array 200" has the same length 203 and width 205 as the single crystal illustrated in FIG. 4.

Each piezoelectric element in the piezoelectric array of the present disclosure may have individual electrical attachments (i.e. electrodes), so that each piezoelectric element can be individually controlled for frequency and power. These elements can share a common ground electrode. This configuration allows for not only the generation of a multi-dimensional acoustic standing wave, but also improved control of the acoustic standing wave.

The piezoelectric array can be formed from a monolithic piezoelectric crystal by making cuts across one surface so as to divide the surface of the piezoelectric crystal into separate elements. The cutting of the surface may be performed through the use of a saw, an end mill, or other means to remove material from the surface and leave discrete elements of the piezoelectric crystal between the channels/grooves that are thus formed.

Figure 21:
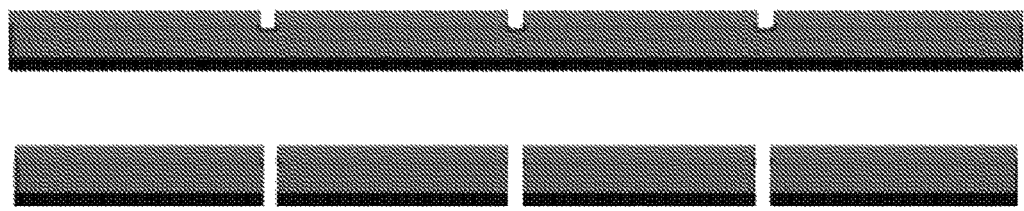
FIG. 21 is a picture illustrating a kerfed crystal (top) versus a transducer array that has piezoelectric elements joined together by a potting material (bottom).

As explained above, a potting material may be incorporated into the channels/grooves between the elements to form a composite material. For example, the potting material can be a polymer, such as epoxy. In particular embodiments, the piezoelectric elements 208 are individually physically isolated from each other. This structure can be obtained by filling the channels 210 with the potting material, then cutting, sanding or grinding the outer surface 204 down to the channels. As a result, the piezoelectric elements are joined to each other through the potting material, and each element is an individual component of the array. Put another way, each piezoelectric element is physically separated from surrounding piezoelectric elements by the potting material. FIG. 21 is a cross-sectional view comparing these two embodiments. On top, a crystal as illustrated in FIG. 5 is shown. The crystal is kerfed into four separate piezoelectric elements 208 on the inner surface 202, but the four elements share a common outer surface 204. On the bottom, the four piezoelectric elements 208 are physically isolated from each other by potting material 212. No common surface is shared between the four elements.

In the present systems, the system is operated at a voltage such that the particles are trapped in the ultrasonic standing wave, i.e., remain in a stationary position. The particles are collected in along well defined trapping lines, separated by half a wavelength. Within each nodal plane, the particles are trapped in the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. In systems using typical transducers, the radial or lateral component of the acoustic radiation force is typically several orders of magnitude smaller than the axial component of the acoustic radiation force. However, the lateral force in the devices of the present disclosure can be significant, on the same order of magnitude as the axial force component, and is sufficient to overcome the fluid drag force at linear velocities of up to 1 cm/s. As discussed above, the lateral force can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage.

During operation, the piezoelectric arrays of the present disclosure can be driven so that the piezoelectric elements are in phase with each other. In other words, each piezoelectric element creates a multi-dimensional acoustic standing wave that has the same frequency and no time shift. In other embodiments, the piezoelectric elements can be out of phase with each other, i.e. there is a different frequency or time shift, or they have a different phase angle. As described further below, in more specific embodiments the elements in the array are arranged in groups or sets that are out of phase by multiples of 90° (i.e. 90° and/or) 180°.

In embodiments, the pulsed voltage signal driving the transducer can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

Figure 7:
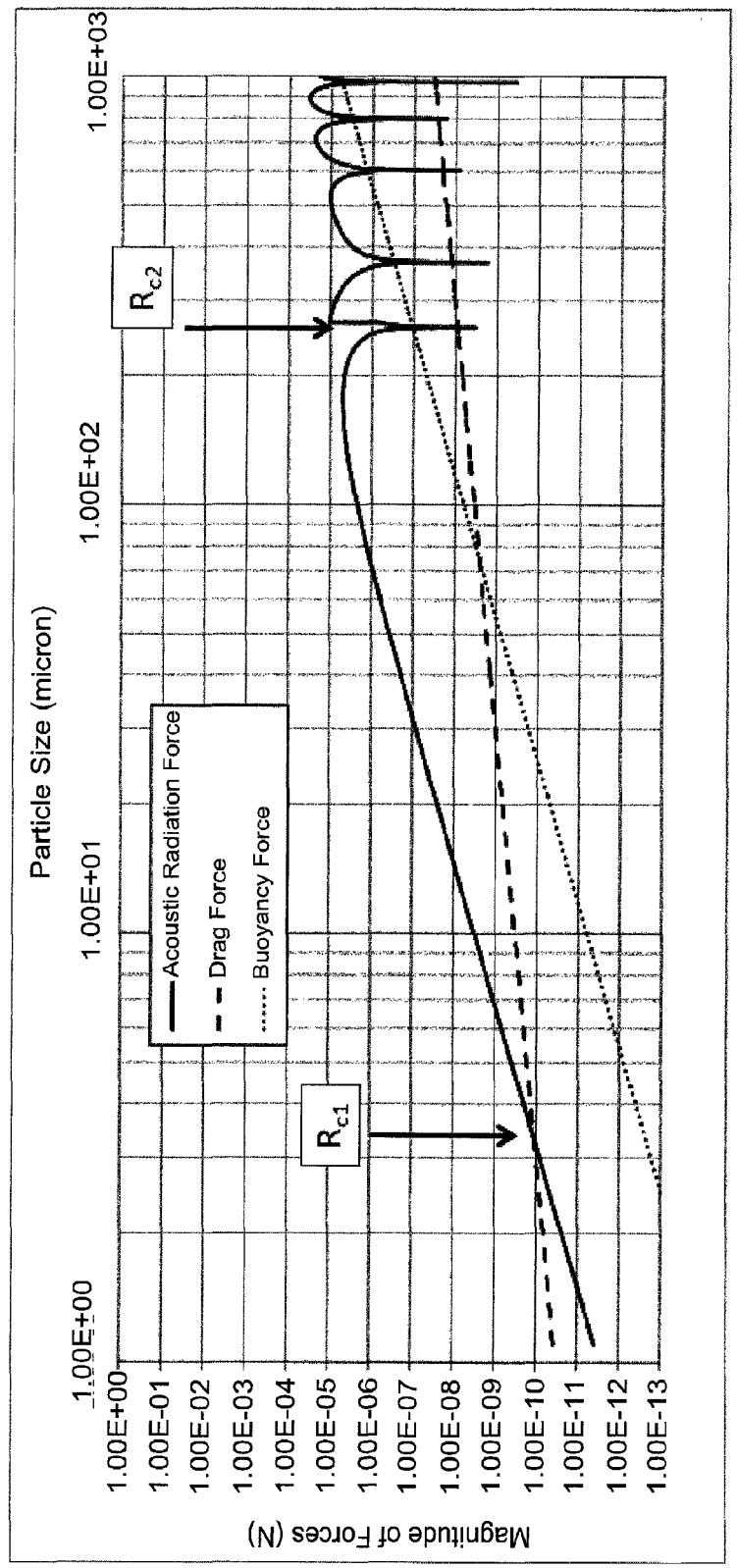
FIG. 7 is a graph showing the relationship of the acoustic radiation force, gravity/buoyancy force, and Stokes' drag force to particle size. The horizontal axis is in microns (μm) and the vertical axis is in Newtons (N).

FIG. 7 is a lin-log graph (linear y-axis, logarithmic x-axis) that shows the calculated scaling of the acoustic radiation force, fluid drag force, and buoyancy force with particle radius. The buoyancy force is applicable to negative contrast factor particles, such as oil particles in this example. The calculated buoyancy force may include elements of gravity forces. In examples using positive contrast factor particles, which may be some types of cells, a line indicating gravity forces is used in a graph for such positive contrast factor particles showing acoustic radiation force and fluid drag force. In the present example illustrated in FIG. 7 calculations are done for a typical SAE-30 oil droplet used in experiments. The buoyancy force is a particle volume dependent force, e.g., proportional to the radius cubed, and is relatively negligible for particle sizes on the order of a micron, but grows, and becomes significant for particle sizes on the order of hundreds of microns. The fluid drag force scales linearly with fluid velocity, e.g., proportional to the radius squared, and typically exceeds the buoyancy force for micron sized particles, but is less influential for larger sized particles on the order of hundreds of microns. The acoustic radiation force scaling acts differently than the fluid drag force or the buoyancy force. When the particle size is small, the acoustic trapping force scales with the cube of the particle radius (volume) of the particle at a close to linear rate. Eventually, as the particle size grows, the acoustic radiation force no longer increases linearly with the cube of the particle radius. As the particle size continues to increase, the acoustic radiation force rapidly diminishes and, at a certain critical particle size, is a local minimum. For further increases of particle size, the radiation force increases again in magnitude but with opposite phase (not shown in the graph). This pattern repeats for increasing particle sizes. The particle size to acoustic radiation force relationship is at least partially dependent on the wavelength or frequency of the acoustic standing wave. For example, as a particle increases to a half-wavelength size, the acoustic radiation force on the particle decreases. As a particle size increases to greater than a half-wavelength and less than a full wavelength, the acoustic radiation force on the particle increases.

Initially, when a suspension is flowing through the acoustic standing wave with primarily small micron sized particles, the acoustic radiation force balances the combined effect of fluid drag force and buoyancy force to trap a particle in the standing wave. In FIG. 7, trapping occurs for a particle size of about 3.5 micron, labeled as $R_{c1}$. In accordance with the graph in FIG. 7, as the particle size continues to increase beyond $R_{c1}$, larger particles are trapped, as the acoustic radiation force increases compared to the fluid drag force. As small particles are trapped in the standing wave, particle coalescence/clumping/aggregation/agglomeration takes place, resulting in continuous growth of effective particle size. Other, smaller particles continue to be driven to trapping sites in the standing wave as the larger particles are held and grow in size, contributing to continuous trapping. As the particle size grows, the acoustic radiation force on the particle increases, until a first region of particle size is reached. As the particle size increases beyond the first region, the acoustic radiation force on the particle begins to decrease. As particle size growth continues, the acoustic radiation force decreases rapidly, until the buoyancy force becomes dominant, which is indicated by a second critical particle size, Ra, at which size the particles rise or sink, depending on their relative density or acoustic contrast factor with respect to the host fluid. As the particles rise or sink and leave the antinode (in the case of negative contrast factor) or node (in the case of positive contrast factor) of the acoustic standing wave, the acoustic radiation force on the particles may diminish to a negligible amount. The acoustic radiation force continues to trap small and large particles, and drive the trapped particles to a trapping site, which is located at a pressure antinode in this example. The smaller particle sizes experience a reduced acoustic radiation force, which, for example, decreases to that indicated near point $R_{c1}$. As other particles are trapped and coalesce, clump, aggregate, agglomerate and/or cluster together at the node or antinode of the acoustic standing wave, effectively increasing the particle size, the acoustic radiation force increases and the cycle repeats. All of the particles may not drop out of the acoustic standing wave, and those remaining particles may continue to grow in size. Thus, FIG. 7 explains how small particles can be trapped continuously in a standing wave, grow into larger particles or clumps, and then eventually rise or settle out because of the relationship between buoyancy force, drag force and acoustic radiation force with respect to particle size.

The size, shape, and thickness of the transducer determine the transducer displacement at different frequencies of excitation, which in turn affects oil separation efficiency. Typically, the transducer is operated at frequencies near the thickness resonance frequency (half wavelength). Gradients in transducer displacement typically result in more places for oil to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 8:
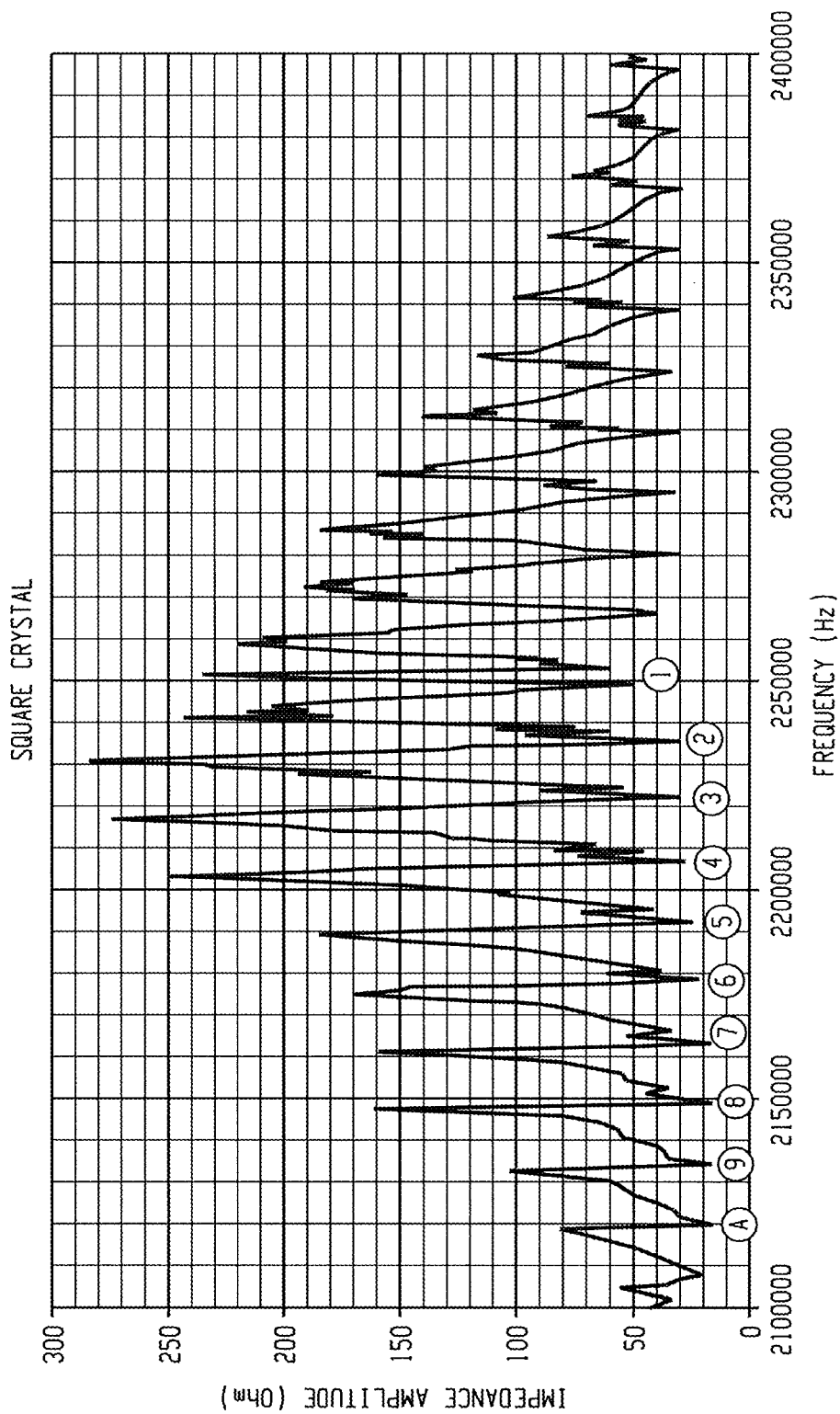
FIG. 8 is a graph of electrical impedance amplitude versus frequency for a square transducer driven at different frequencies.

FIG. 8 shows the measured electrical impedance amplitude of a 1" square PZT-8 2-MHz transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

To investigate the effect of the transducer displacement profile on acoustic trapping force and oil separation efficiencies, an experiment was repeated ten times, with all conditions identical except for the excitation frequency. Ten consecutive acoustic resonance frequencies, indicated by circled numbers 1-9 and letter A on FIG. 8, were used as excitation frequencies. These oscillations in the impedance correspond to the resonance of the acoustophoretic system. With the length of the acoustophoretic system being 2", the oscillations are spaced about 15 kHz apart. The conditions were experiment duration of 30 min, a 1000 ppm oil concentration of approximately 5-micron SAE-30 oil droplets, a flow rate of 500 ml/min, and an applied power of 20 W in a 1-inch wide×2-inch long cross-section.

As the emulsion passed by the transducer, the trapping lines of oil droplets were observed and characterized. The characterization involved the observation and pattern of the number of trapping lines across the fluid channel, as shown in FIG. 9A, for seven of the ten resonance frequencies identified in FIG. 8.

FIG. 9B shows an isometric view of the system in which the trapping line locations are being determined. FIG. 9C is a view of the system as it appears when looking down the inlet, along arrow 114. FIG. 9D is a view of the system as it appears when looking directly at the transducer face, along arrow 116. The trapping lines shown in FIGS. 9B-9D are those produced at frequency 4 in FIG. 8 and FIG. 9A.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines.

Figure 10A:
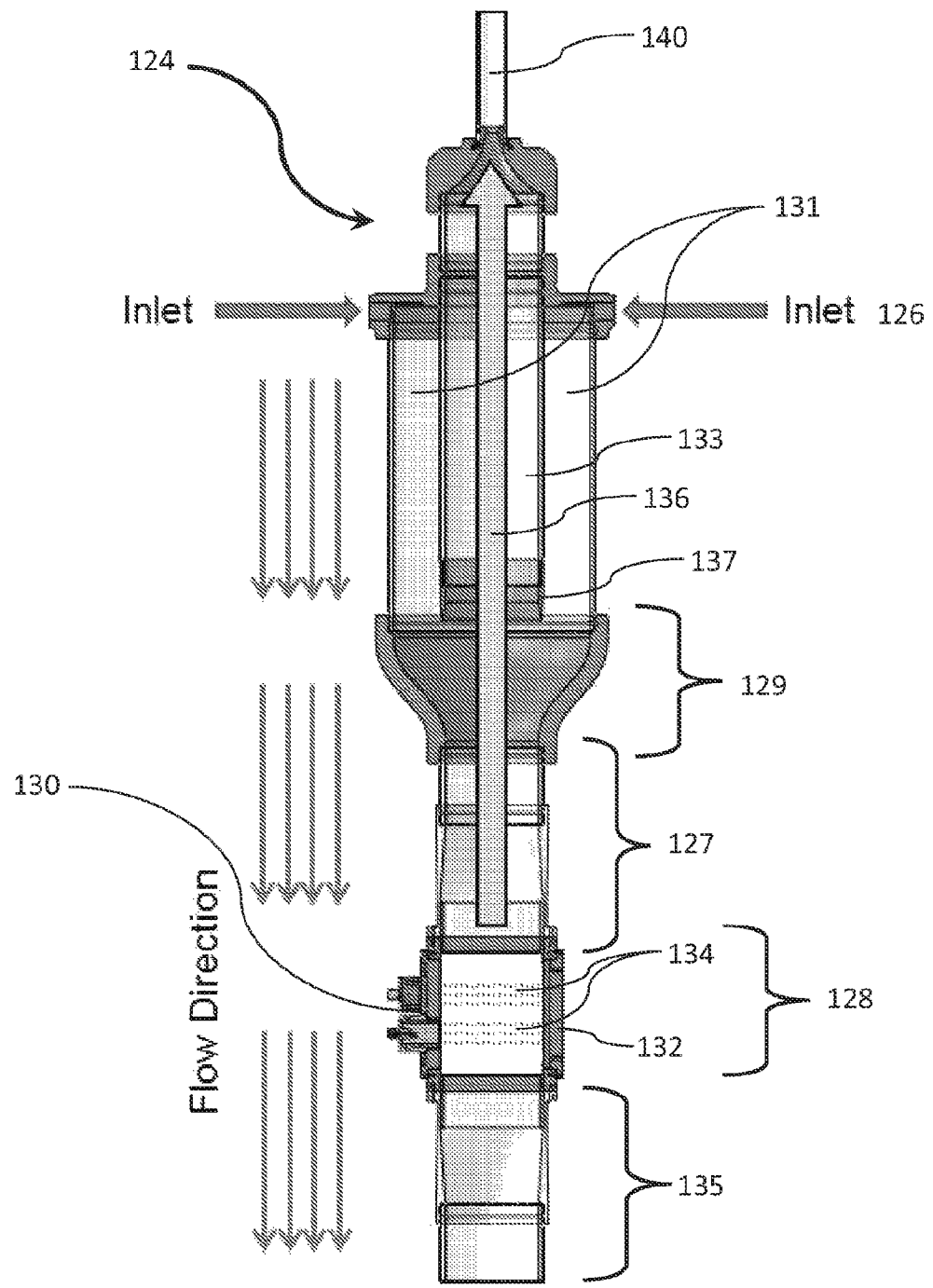
FIG. 10A shows an acoustophoretic separator for separating buoyant materials.

Table 1 summarizes the findings from an oil trapping experiment using a system similar to FIG. 10A. An important conclusion is that the oil separation efficiency of the acoustic separator is directly related to the mode shape of the transducer. Higher order displacement profiles generate larger acoustic trapping forces and more trapping lines resulting in better efficiencies. A second conclusion, useful for scaling studies, is that the tests indicate that capturing 5 micron oil droplets at 500 ml/min implies 10 Watts of power per square-inch of transducer area per 1" of acoustic beam span. The main dissipation is that of thermo-viscous absorption in the bulk volume of the acoustic standing wave. The cost of energy associated with this flow rate is 0.500 kWh per cubic meter.

TABLE 1

Trapping Pattern Capture Efficiency Study

| Resonance Peak Location | Total Power Input (Watts) | # of Trapping Lines | Flow rate (ml/min) | Duration (min) | Capture Efficiency (%) |
|---|---|---|---|---|---|
| 4 | 20 | 9 | 500 | 30 | 91% |
| 8 | 20 | 5 | 500 | 30 | 58% |
| A | 20 | 4 | 500 | 30 | 58% |
| 9 | 20 | 2 | 500 | 30 | 37% |

A 4" by 2.5" flow cross sectional area intermediate scale apparatus 124 for separating a host fluid from a buoyant fluid or particulate is shown in FIG. 10A. The acoustic path length is 4". The apparatus is shown here in an orientation where the flow direction is downwards, which is used for separating less-dense particles from the host fluid. However, the apparatus may be essentially turned upside down to allow separation of particles which are heavier than the host fluid. Instead of a buoyant force in an upward direction, the weight of the agglomerated particles due to gravity pulls them downward. It should be noted that this embodiment is depicted as having an orientation in which fluid flows vertically. However, it is also contemplated that fluid flow may be in a horizontal direction, or at an angle.

A particle-containing fluid enters the apparatus through inlets 126 into an annular plenum 131. The annular plenum has an annular inner diameter and an annular outer diameter. It is noted that the term "annular" is used here to refer to the area between two shapes, and the plenum does not need to be circular. Two inlets are visible in this illustration, though it is contemplated that any number of inlets may be provided as desired. In particular embodiments, four inlets are used. The inlets are radially opposed and oriented.

A contoured nozzle wall 129 reduces the outer diameter of the flow path in a manner that generates higher velocities near the wall region and reduces turbulence, producing near plug flow as the fluid velocity profile develops, i.e. the fluid is accelerated downward in the direction of the centerline with little to no circumferential motion component and low flow turbulence. This chamber flow profile is desirable for acoustic separation and particle collection. The fluid passes through connecting duct 127 and into a flow/separation chamber 128. As seen in the zoomed-in contoured nozzle 129 in FIG. 10B, the nozzle wall also adds a radial motion component to the suspended particles, moving the particles closer to the centerline of the apparatus and generating more collisions with rising, buoyant agglomerated particles. This radial motion will allow for optimum scrubbing of the particles from the fluid in the connecting duct 127 prior to reaching the separation chamber. The contoured nozzle wall 129 directs the fluid in a manner that generates large scale vortices at the entrance of the collection duct 133 to also enhance particle collection. Generally, the flow area of the device 124 is designed to be continually decreasing from the annular plenum 131 to the separation chamber 128 to assure low turbulence and eddy formation for better particle separation, agglomeration, and collection. The nozzle wall has a wide end and a narrow end. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension.

Returning to FIG. 10A, the flow/separation chamber 128 includes a transducer array 130 and reflector 132 on opposite sides of the chamber. In use, multi-dimensional standing waves 134 are created between the transducer array 130 and reflector 132. These standing waves can be used to agglomerate particles, and this orientation is used to agglomerate particles that are buoyant (e.g. oil). Fluid, containing residual particles, then exits through flow outlet 135.

As the buoyant particles agglomerate, they eventually overcome the combined effect of the fluid flow drag forces and acoustic radiation force, and their buoyant force 136 is sufficient to cause the buoyant particles to rise upwards. In this regard, a collection duct 133 is surrounded by the annular plenum 131. The larger particles will pass through this duct and into a collection chamber 140. This collection chamber can also be part of an outlet duct. The collection duct and the flow outlet are on opposite ends of the apparatus.

It should be noted that the buoyant particles formed in the separation chamber 128 subsequently pass through the connecting duct 127 and the nozzle wall 129. This arrangement causes the incoming flow from the annular plenum to flow over the rising agglomerated particles due to the inward radial motion imparted by the nozzle wall.

The transducer setup of the present disclosure creates a three-dimensional pressure field which includes standing waves perpendicular to the fluid flow. The pressure gradients are large enough to generate acoustophoretic forces in a lateral direction, e.g., orthogonal to the standing wave direction (i.e., the acoustophoretic forces are parallel to the fluid flow direction) which are of the same order of magnitude as the acoustophoretic forces in the wave direction. These forces permit enhanced particle trapping, clumping and collection in the flow chamber and along well-defined trapping lines, as opposed to merely trapping particles in collection planes as in conventional devices. The particles have significant time to move to nodes or anti-nodes of the standing waves, generating regions where the particles can concentrate, agglomerate, and/or coalesce, and then buoyancy/gravity separate.

In some embodiments, the fluid flow has a Reynolds number of up to 1500, i.e. laminar flow is occurring. For practical application in industry, the Reynolds number is usually from 10 to 1500 for the flow through the system. The particle movement relative to the fluid motion generates a Reynolds number much less than 1.0. The Reynolds number represents the ratio of inertial flow effects to viscous effects in a given flow field. For Reynolds numbers below 1.0, viscous forces are dominant in the flow field. This situation results in significant damping where shear forces are predominant throughout the flow. This flow where viscous forces are dominant is called Stokes flow. The flow of molasses is an example. Wall contouring and streamlining have very little importance under such conditions. These characteristics are associated with the flow of very viscous fluids or the flow in very tiny passages, like MEMS devices. Inlet contouring has little importance. The flow of the particles relative to the fluid in an acoustophoretic particle separator will be Stokes flow because both the particle diameters and the relative velocities between the particles and fluid are very small. On the other hand, the Reynolds number for the flow through the system will be much greater than 1.0 because the fluid velocity and inlet diameter are much larger.

For Reynolds numbers much greater than 1.0, viscous forces are dominant where the flow is in contact with the surface. This viscous region near the surface is called a boundary layer and was first recognized by Ludwig Prandtl. In duct flow, the flow will be laminar if the Reynolds number is significantly above 1.0 and below 2300 for fully developed flow in the duct. The wall shear stress at the wall will diffuse into the stream with distance. At the inlet of the duct, flow velocity starts off uniform. As the flow moves down the duct, the effect of wall viscous forces will diffuse inward towards the centerline to generate a parabolic velocity profile. This parabolic profile will have a peak value that is twice the average velocity. The length of duct for the parabolic profile to develop is a function of the Reynolds number. For a Reynolds number of 20, which is typical for CHO operation, the development length will be 1.2 duct diameters. Thus, fully developed flow happens very quickly. This peak velocity in the center can be detrimental to acoustic particle separation. Also, at laminar flow Reynolds numbers turbulence, can occur and flow surface contouring is very important in controlling the flow. For these reasons, the separator was designed with an annular inlet plenum and collector tube.

Figure 10B:
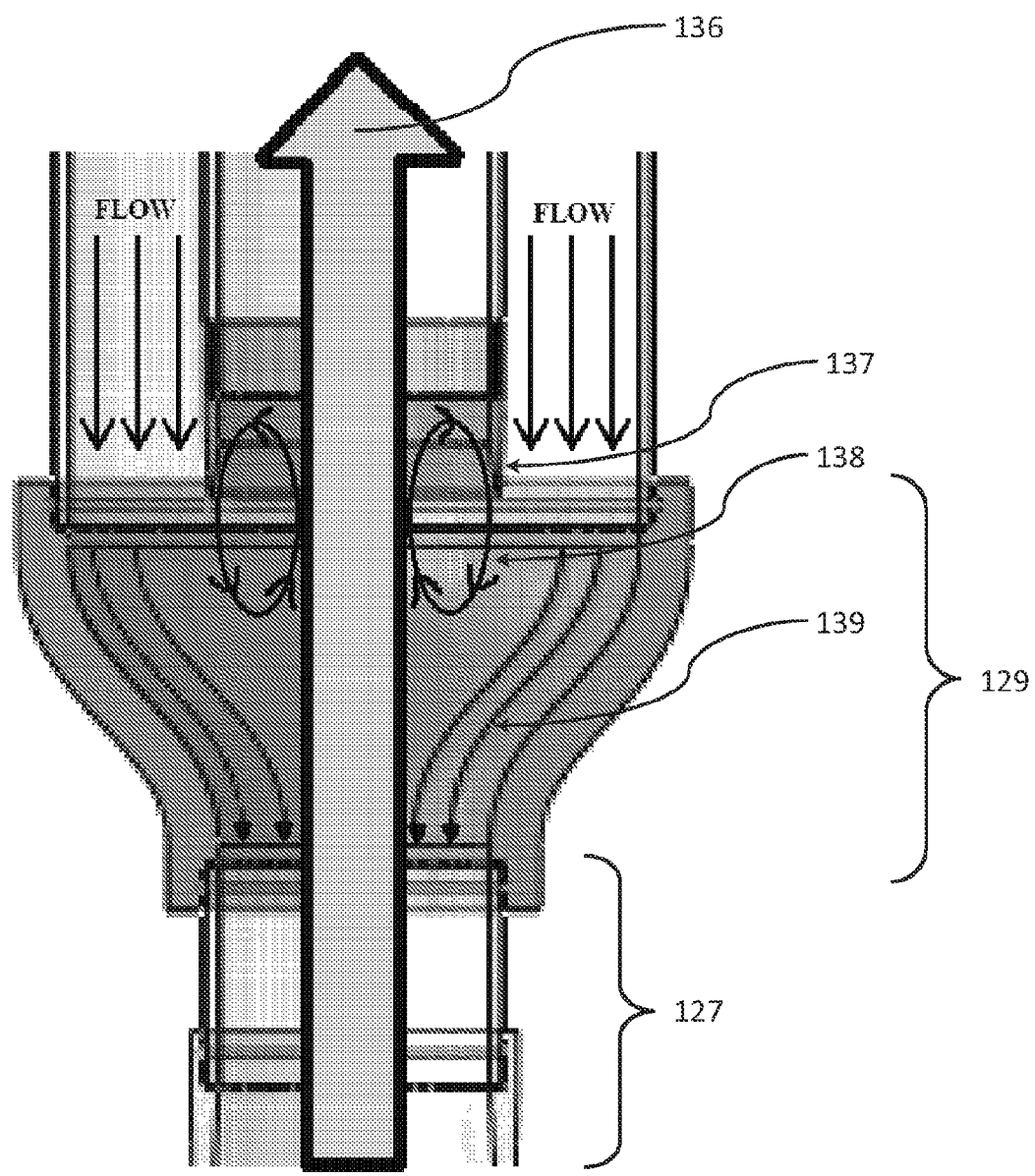
FIG. 10B is a magnified view of fluid flow near the intersection of the contoured nozzle wall 129 and the collection duct 137.

The large annular plenum is followed by an inlet wall nozzle that accelerates and directs the fluid inward toward the centerline as shown in FIG. 10B. The wall contour will have a large effect on the profile. The area convergence increases the flow average velocity, but it is the wall contour that determines the velocity profile. The nozzle wall contour will be a flow streamline, and is designed with a small radius of curvature in the separator.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer 130 and the reflector 132. Hot spots are located at the minima of acoustic radiation potential. Such hot spots represent particle collection locations.

One application of the acoustophoretic device is the separation of a biological therapeutic protein from the biologic cells that produce the protein. In this regard, current methods of separation use filtration or centrifugation, either of which can damage cells, releasing protein debris and enzymes into the purification process and increasing the load on downstream portions of the purification system. It is desirable to be able to process volumes having higher cell densities, because this permits collection of larger amounts of the therapeutic protein and better cost efficiencies.

Figure 11A:
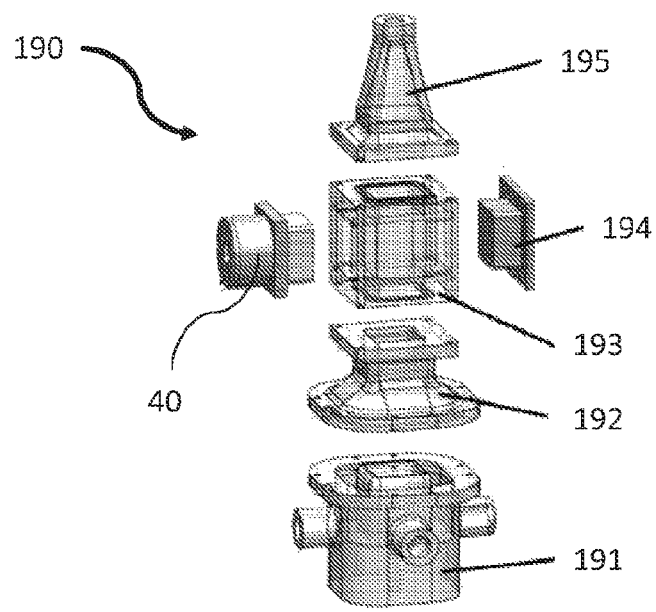
FIG. 11A shows an exploded view of an acoustophoretic separator used in Bio-Pharma applications.
Figure 11B:
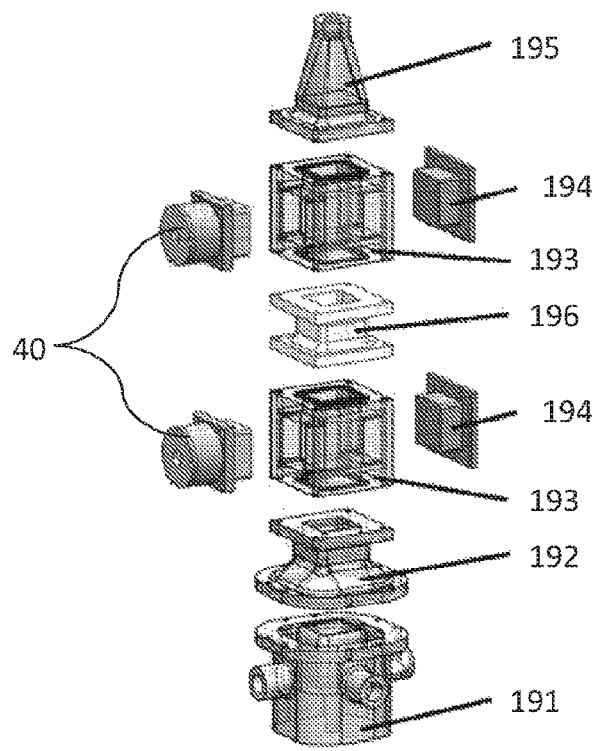
FIG. 11B shows an exploded view of a stacked acoustophoretic separator with two acoustic chambers.

FIG. 11A and FIG. 11B are exploded views showing the various parts of acoustophoretic separators. FIG. 11A has only one separation chamber, while FIG. 11B has two separation chambers.

Referring to FIG. 11A, fluid enters the separator 190 through a four-port inlet 191. An annular plenum is also visible here. A transition piece 192 is provided to create plug flow through the separation chamber 193. This transition piece includes a contoured nozzle wall, like that described above in FIG. 10A, which has a curved shape. A transducer 40 and a reflector 194 are located on opposite walls of the separation chamber. Fluid then exits the separation chamber 193 and the separator through outlet 195. The separation chamber has a rectangular-shaped flow path geometry.

FIG. 11B has two separation chambers 193. A system coupler 196 is placed between the two chambers 193 to join them together.

Acoustophoretic separation has been tested on different lines of Chinese hamster ovary (CHO) cells. In one experiment, a solution with a starting cell density of 8.09×10$^6$ cells/mL, a turbidity of 1,232 NTU, and cell viability of roughly 75% was separated using a system as depicted in FIG. 11A. The transducers were 2 MHz crystals, run at approximately 2.23 MHz, drawing 24-28 Watts. A flow rate of 25 mL/min was used. The result of this experiment is shown in FIG. 12A.

In another experiment, a solution with a starting cell density of 8.09×10$^6$ cells/mL, a turbidity of 1,232 NTU, and cell viability of roughly 75% was separated. This CHO cell line had a bi-modal particle size distribution (at size 12 µm and 20 µm). The result is shown in FIG. 12B.

Figure 12A:
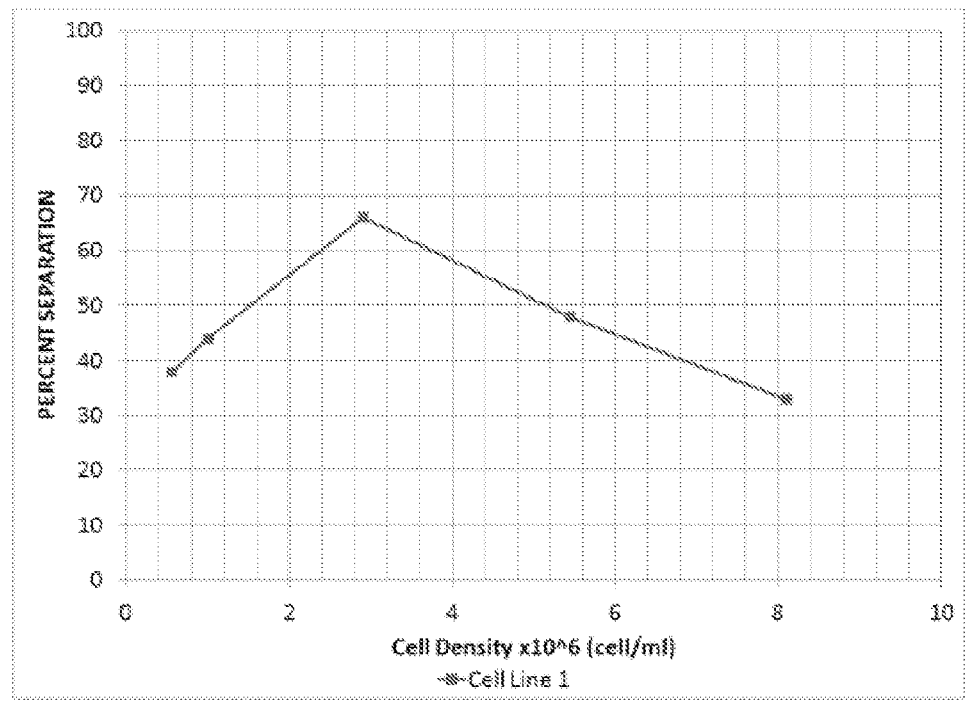
FIG. 12A is a graph showing the efficiency of removing cells from a medium using a Beckman Coulter Cell Viability Analyzer for one experiment.
Figure 12B:
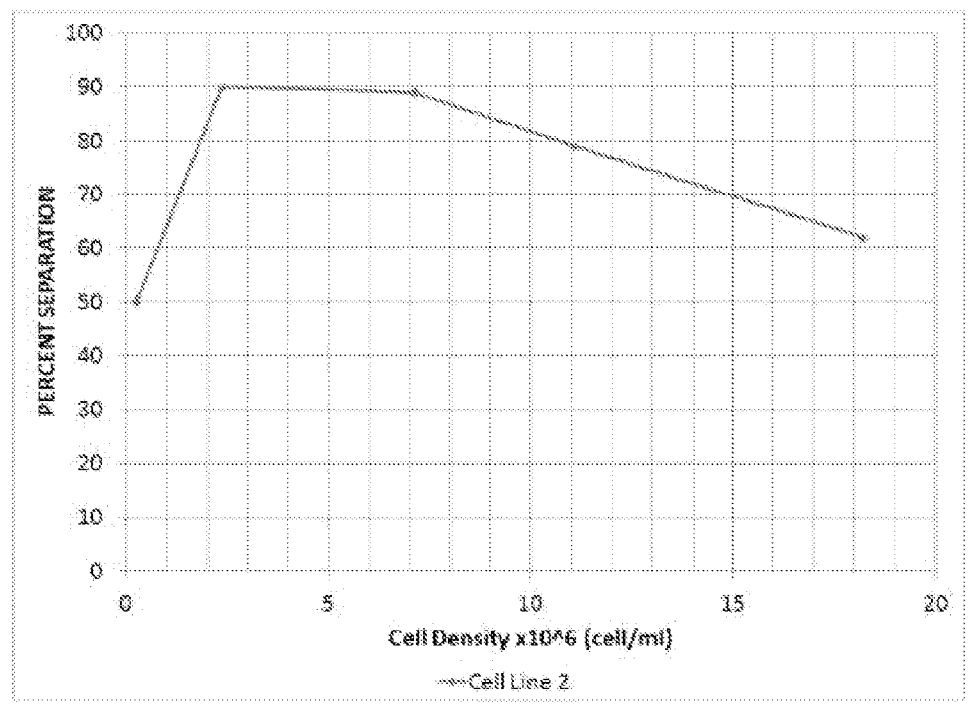
FIG. 12B is a graph showing the efficiency of removing cells from a medium using a Beckman Coulter Cell Viability Analyzer for another experiment.

FIG. 12A and FIG. 12B were produced by a Beckman Coulter Cell Viability Analyzer. Other tests revealed that frequencies of 1 MHz and 3 MHz, were not as efficient as 2 MHz at separating the cells from the fluid.

In other tests at a flow rate of 10 L/hr, 99% of cells were captured with a confirmed cell viability of more than 99%. Other tests at a flow rate of 50 mL/min (i.e. 3 L/hr) obtained a final cell density of 3×106 cells/mL with a viability of nearly 100% and little to no temperature rise. In yet other tests, a 95% reduction in turbidity was obtained at a flow rate of 6 L/hr.

Testing on the scaled unit shown in FIG. 10A-10B was performed using yeast as a simulant for CHO for the biological applications. For these tests, at a flow rate of 15 L/hr, various frequencies were tested as well as power levels. Table 2 shows the results of the testing.

TABLE 2

2.5" × 4" System results at 15 L/hr Flow rate

| Frequency (MHz) | 30 Watts | 37 Watts | 45 Watts |
|---|---|---|---|
| 2.2211 | 93.9 | 81.4 | 84.0 |
| 2.2283 | 85.5 | 78.7 | 85.4 |
| 2.2356 | 89.1 | 85.8 | 81.0 |
| 2.243 | 86.7 | — | 79.6 |

In biological applications, many parts, e.g. the tubing leading to and from the housing, inlets, exit plenum, and entrance plenum, may all be disposable, with only the transducer and reflector to be cleaned for reuse. Avoiding centrifuges and filters allows better separation of the CHO cells without lowering the viability of the cells. The form factor of the acoustophoretic separator is also smaller than a filtering system, allowing the CHO separation to be miniaturized. The transducers may also be driven to create rapid pressure changes to prevent or clear blockages due to agglomeration of CHO cells. The frequency of the transducers may also be varied to obtain optimal effectiveness for a given power.

The following examples are provided to illustrate the apparatuses, components, and methods of the present disclosure. The examples are merely illustrative and are not intended to limit the disclosure to the materials, conditions, or process parameters set forth therein.

EXAMPLES

Figure 13:
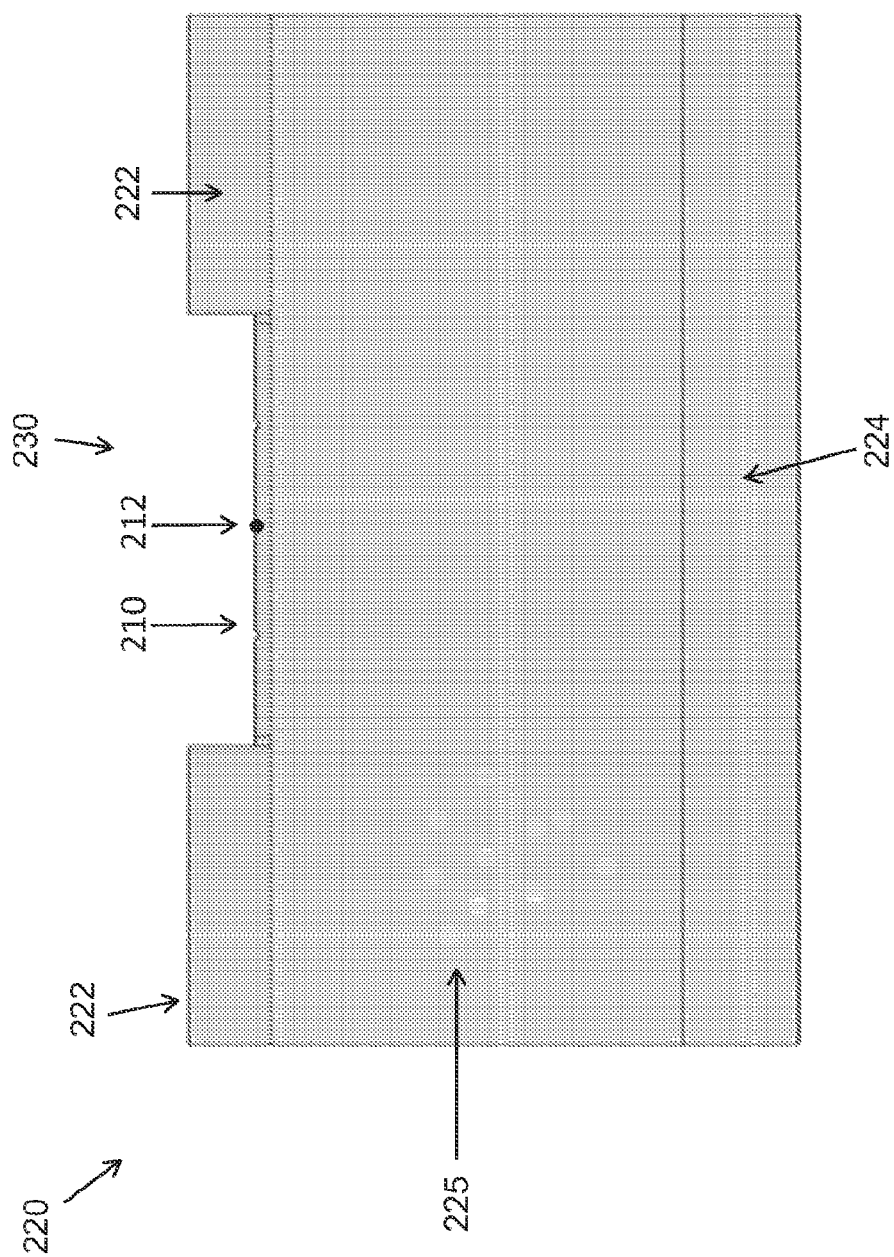
FIG. 13 shows a schematic of a two-dimensional numerical model developed for the simulation of an ultrasonic transducer and transducer array.

A two-dimensional numerical model was developed for the acoustophoretic device using COMSOL simulation software. The model is illustrated in FIG. 13. The device included an aluminum wall 222, and a stainless steel reflector 224 opposite the wall. Embedded in the wall was a piezoelectric transducer 230. As illustrated here, the transducer is in the form of a 4-element piezoelectric array. The wall 222 and the reflector 224 define a flow chamber, with arrow 225 indicating the flow direction of fluid through the chamber. The piezoelectric transducer was in direct contact with the fluid. Channels/kerfs 210 and potting material 212 are also illustrated, though potting material was not used in the simulation.

The simulation software was run, and its output was compared to published data (Barmatz, J. Acoust. Soc. Am. 77, 928, 1985). FIG. 14A compares the acoustic potential U. FIG. 14B compares the x-component of the acoustic radiation force (ARF). FIG. 14C compares the y-component of the ARF. FIG. 14D compares the absolute value of the ARF. In these figures, the published data is on the top, while the numerical model results are on the bottom. As can be seen here, the results of the numerical model match the published data, which validates the numerical model and subsequent calculations made therefrom.

Three different simulations were then run to model the separation of SAE 30 oil droplets from water using three different piezoelectric transducers: a 1-element transducer (i.e. single crystal), a 4-element transducer, and a 5-element transducer. The transducers were operated at the same frequency, and the following parameters were used for the oil and the water: oil particle radius ($R_p$)=10 µm; oil density ($p_p$)=865 kg/m3; speed of sound in oil ($c_p$)=1750 m/sec; particle velocity ($\mu_f$)=0.001 kg/m·sec; water density ($p_f$)=1000 kg/m3; and speed of sound in water ($c_f$)=1500 m/sec.

For the 4-element transducer, each channel had a width of 0.0156 inches and a depth of 0.0100 inches, and each element had a width of 0.2383 inches (total width of the transducer was one inch). For the 5-element transducer, each channel had a width of 0.0156 inches and a depth of 0.0100 inches, and each element had a width of 0.1875 inches.

FIG. 15 shows the simulation of the forces on a particle using the 1-element transducer, which is a two-dimensional representation of PZT crystal 200. FIG. 16 shows the simulation of the forces on a particle using the 4-element transducer, which is a two-dimensional representation of PZT crystal 200'. FIG. 17 shows the simulation of the forces on a particle using the 5-element transducer, which is a two-dimensional representation of PZT crystal 200". Each transducer had the same width, regardless of the number of elements. The amplitude of the multi-dimensional acoustic standing waves generated therefrom are clearly seen (lighter area is higher amplitude than darker area).

Next, simulations were run on a 4-element array to compare the effect of the phase on the waves. The flow rate was 500 mL/min, the Reynolds number of the fluid was 220, the input voltage per element was 2.5 VDC, and the DC power per element was 1 watt. In one simulation, the four elements were in a 0-180-0-180 phase (i.e. out of phase) with respect to each other. In another simulation, the four elements were all in phase with each other. The simulations were then compared to actual experiments conducted with a transducer device having a 4×4 piezoelectric array as in FIG. 18.

Figure 18:
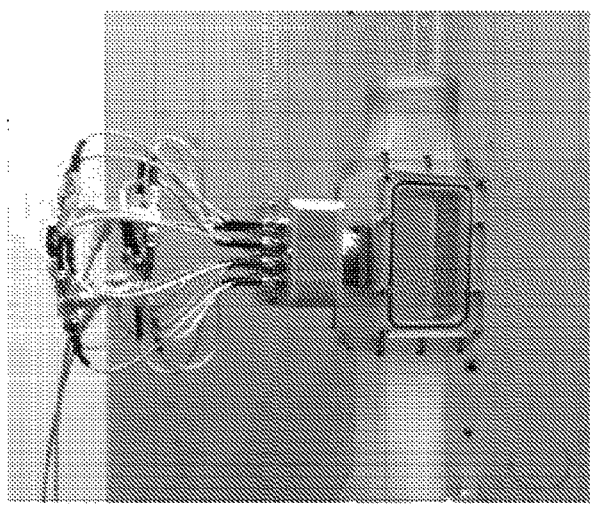
FIG. 18 is a picture of an acoustophoretic setup with a 4×4 piezoelectric array made from a 2 MHz PZT-8 crystal with kerfs made in the crystal, as shown in FIG. 5.
Figures 19, 20:
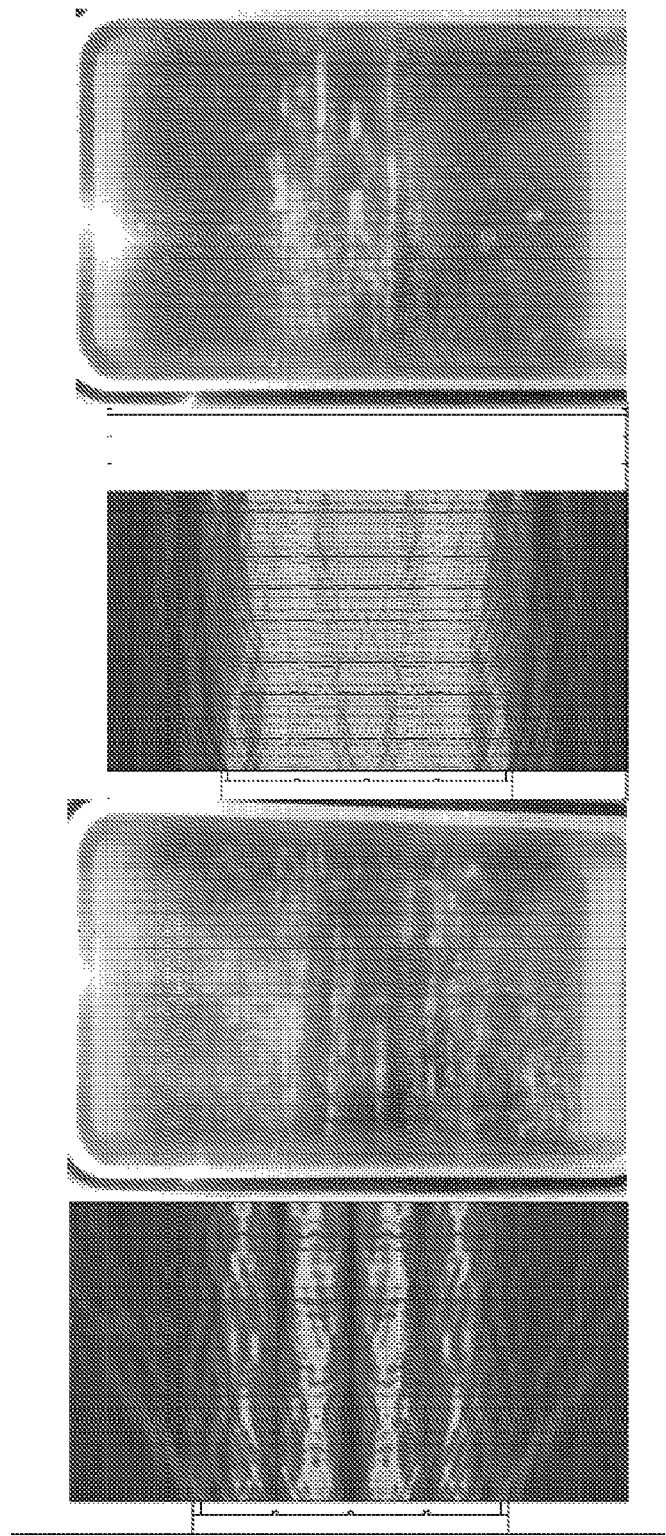
FIG. 19 is a comparison of the simulation of an out-of-phase piezoelectric array with an actual acoustophoretic experiment using the out-of-phase array. For this simulation, out-of-phase refers to the phase angle of the delivered voltage. For out-of-phase testing, the phasing varied from 0°-180°-0°-180° for the numerical model. For the experimental test, the elements were varied in a checkerboard pattern.
FIG. 20 is a comparison of the simulation of an in-phase piezoelectric array with an actual acoustophoretic experiment using the in-phase array. For this simulation, in-phase refers to the phase angle of the delivered voltage. For in-phase testing, the phasing was kept constant between all elements.

FIG. 19 compares the results of the out-of-phase simulation (left) with a picture (right) showing the actual results when an out-of-phase array was used in the transducer device of FIG. 18. The results are very similar. Where the amplitude is high in the simulation, trapped particles are seen in the actual picture.

FIG. 20 compares the results of the in-phase simulation (left) with a picture (right) showing the actual results when an in-phase array was used in the transducer device of FIG. 18. The results are very similar.

Additional numerical models were performed with the 4-element transducer and the 5-element transducer, either in-phase or out-of-phase in different arrangements, as described in Table 3 below, over a frequency sweep of 2.19 MHz to 2.25 MHz, for oil droplets of diameter 20 microns. Out-of-phase means that adjacent elements are excited with different phases.

Figure 22:
FIG. 22 is a diagram showing the out-of-phase modes tested for the 4-element array.
Figure 23:
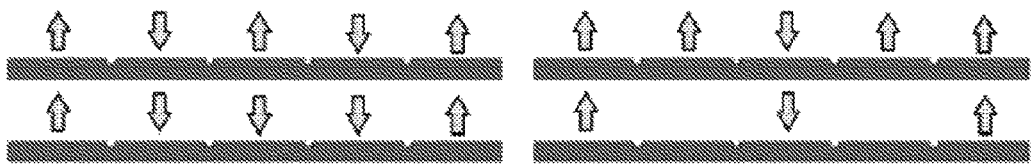
FIG. 23 is a diagram showing the out-of-phase modes tested for the 5-element array.

FIG. 22 is a diagram illustrating the two out-of-phase modes that were simulated for the 4-element array. The left-hand side illustrates the 0-180-0-180 mode, while the right-hand side illustrated the 0-180-180-0 mode. FIG. 23 is a diagram illustrating the four out-of-phase modes that were simulated for the 5-element array. The top left picture illustrates the 0-180-0-180-0 mode. The top right picture illustrates the 0-0-180-0-0 mode. The bottom left picture illustrates the 0-180-180-180-0 mode. The bottom right picture illustrates the 0-90-180-90-0 mode.

The ratio of the lateral (x-axis) force component to the axial (y-axis) force component of the acoustic radiation force was determined over this frequency range, and the range of that ratio is listed in Table 3 below.

TABLE 3

| Transducer | Phase | Ratio Min | Ratio Max |
| --- | --- | --- | --- |
| 1-Element (single crystal) | | ~0.15 | ~0.75 |
| 4-Element Array | In-Phase | ~0.08 | ~0.54 |
| 4-Element Array | (0-180-0-180) | ~0.39 | ~0.94 |
| 4-Element Array | (0-180-180-0) | ~0.39 | ~0.92 |
| 5-Element Array | In-Phase | ~0.31 | ~0.85 |
| 5-Element Array | (0-180-0-180-0) | ~0.41 | ~0.87 |
| 5-Element Array | (0-0-180-0-0) | ~0.41 | ~0.81 |
| 5-Element Array | (0-180-180-180-0) | ~0.40 | ~0.85 |
| 5-Element Array | (0-90-180-90-0) | ~0.38 | ~0.81 |

Figure 24:
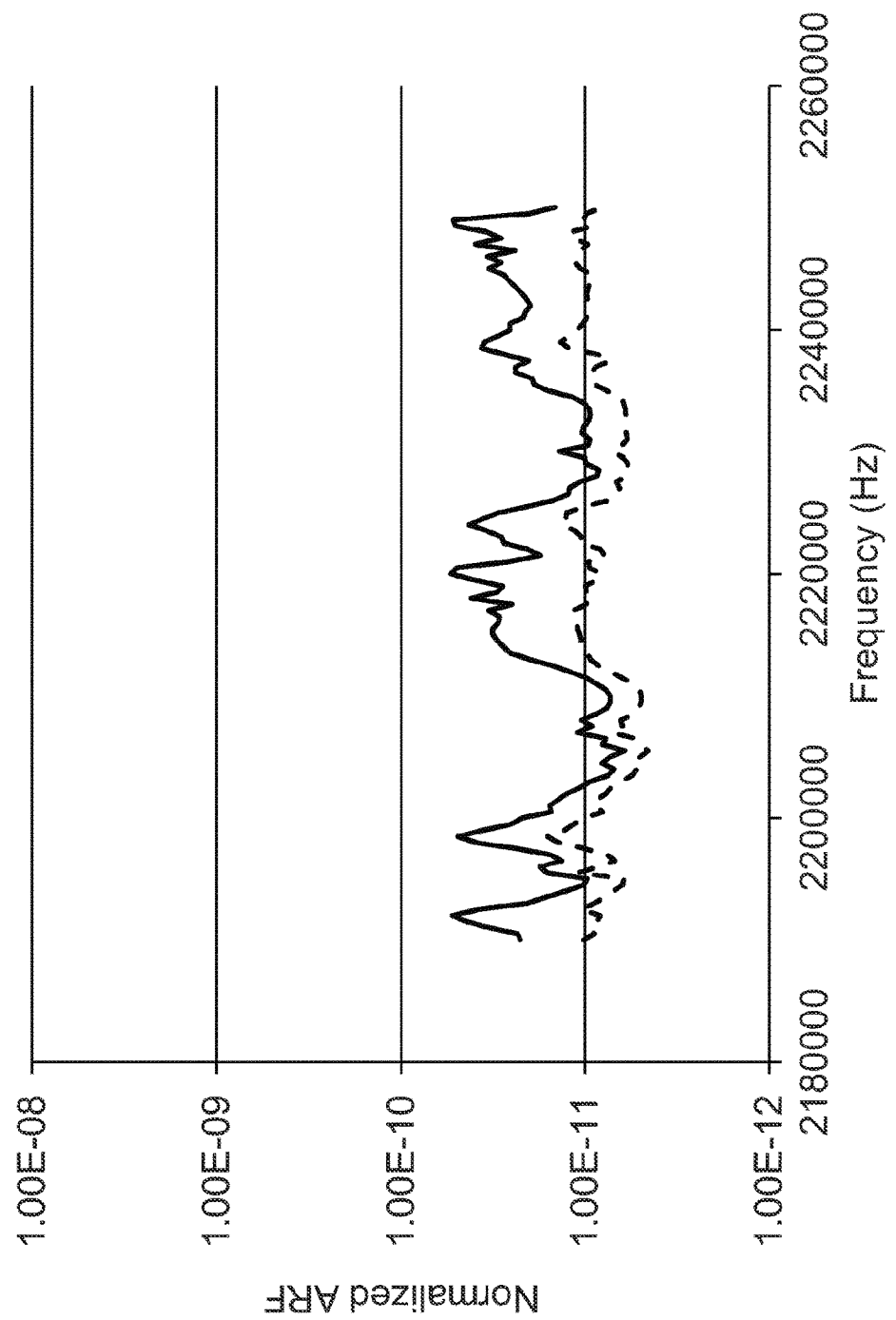
FIG. 24 is a graph showing the normalized acoustic radiation force (ARF) from a monolithic piezoelectric crystal simulation.
Figure 25:
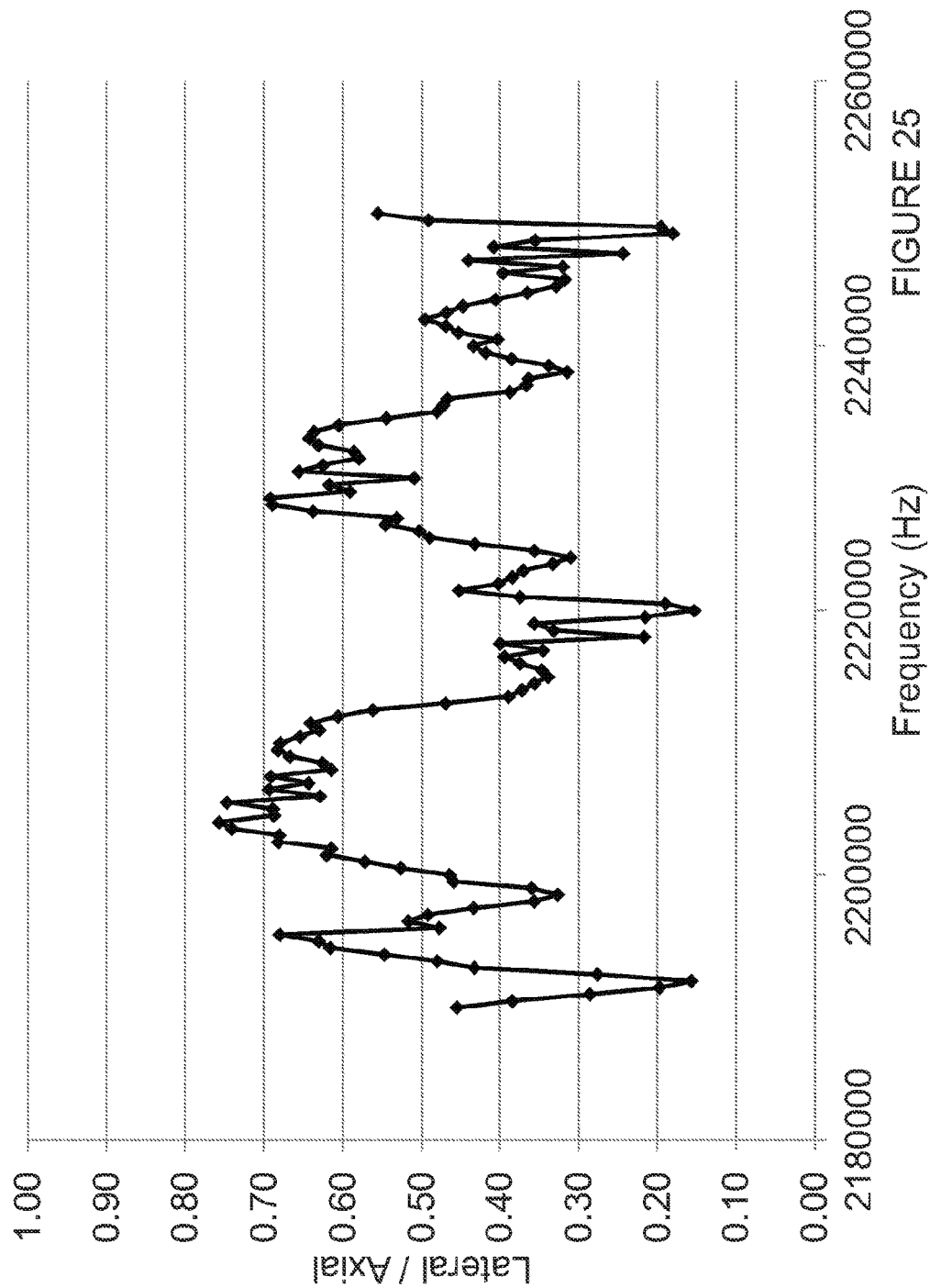
FIG. 25 is a graph showing the ratio of the ARF components (lateral to axial) for a monolithic piezoelectric crystal simulation.
Figure 26:
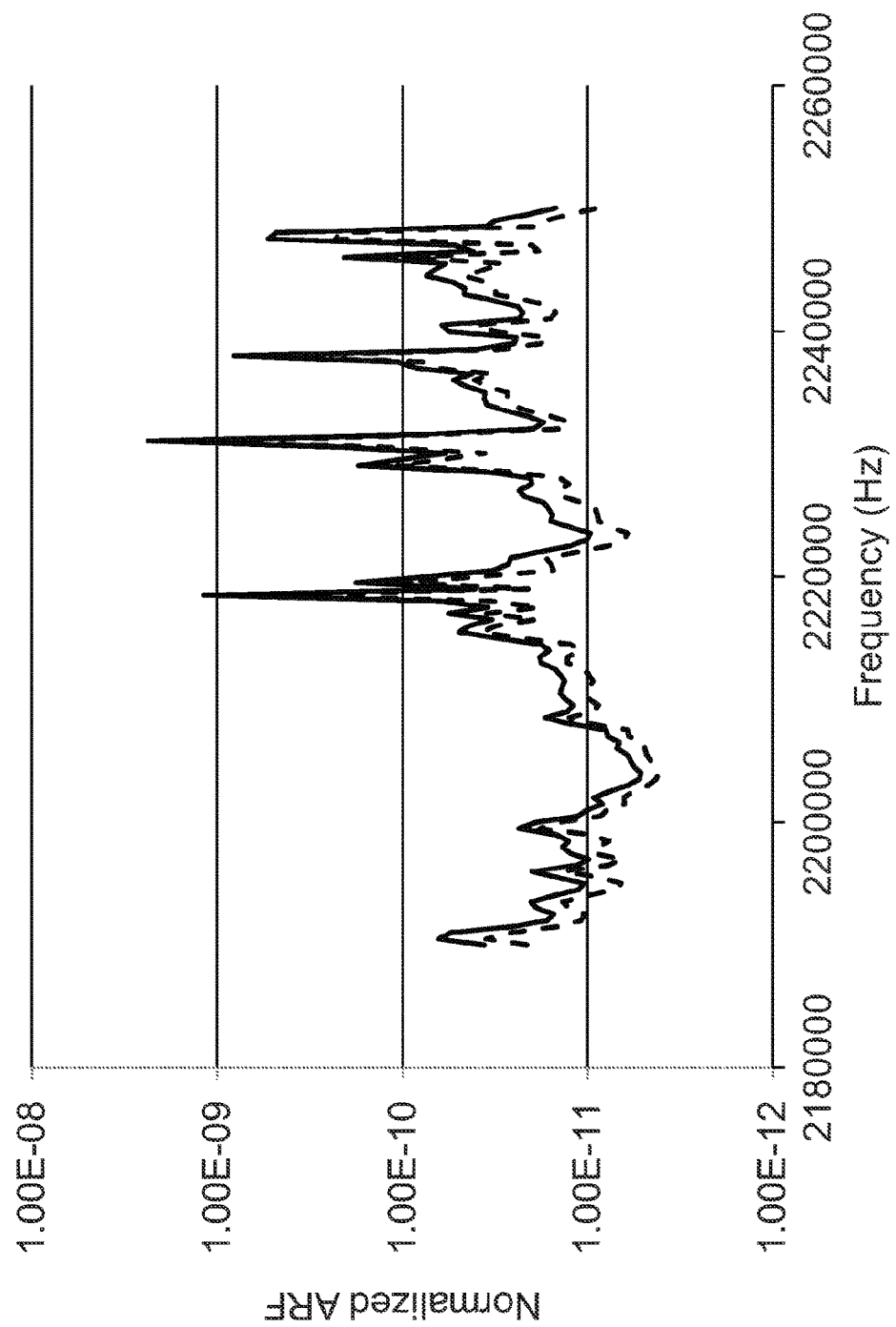
FIG. 26 is a graph showing the normalized acoustic radiation force (ARF) for a 5-element simulation with varying phasing.
Figure 27:
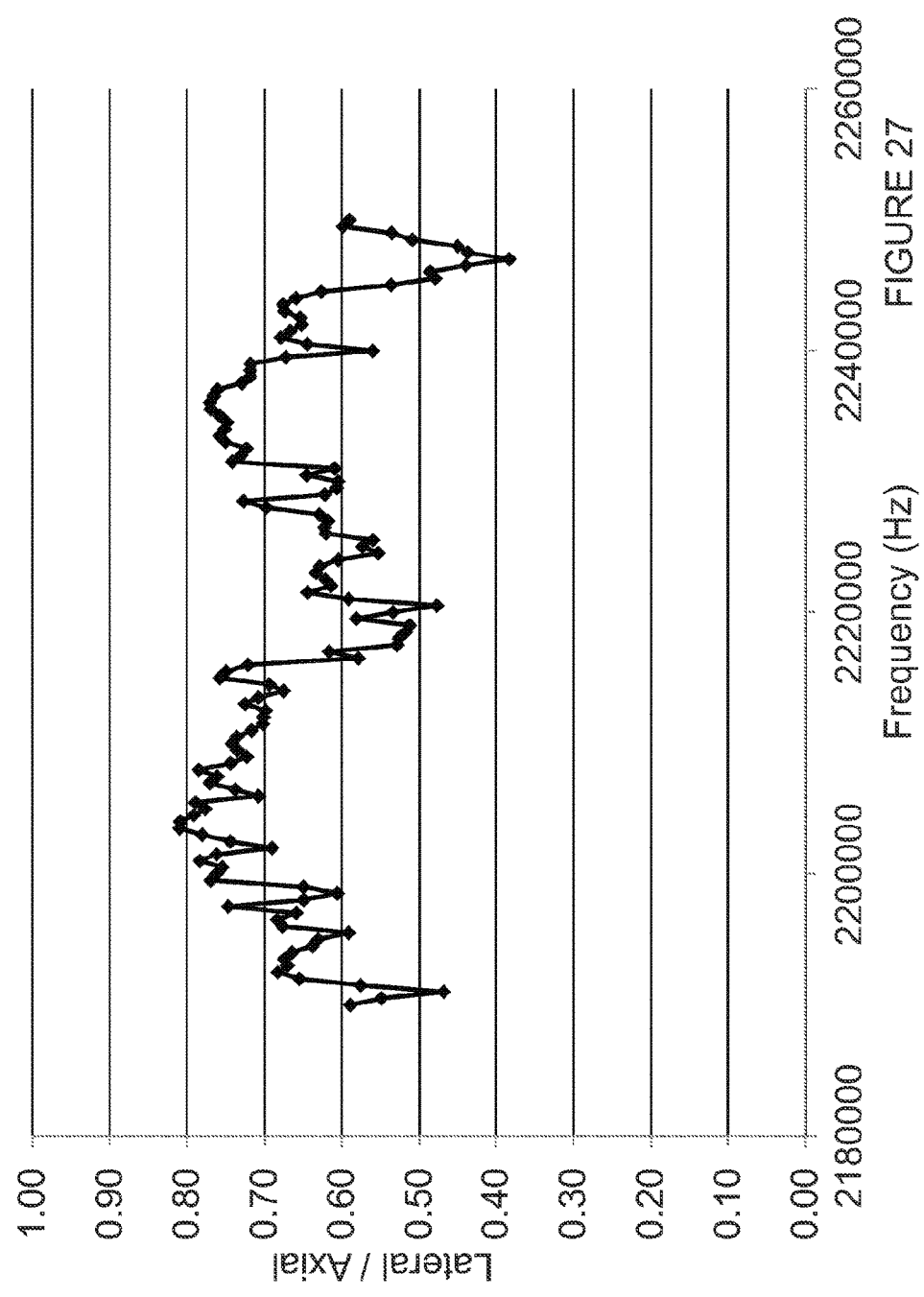
FIG. 27 is a graph showing the ratio of the ARF components (lateral to axial) for the 5-element simulation.

FIG. 24 shows the normalized acoustic radiation force (ARF) from the single piezoelectric crystal simulation. The ARF value was normalized with the real power calculated with the measured voltage and current. FIG. 25 shows the ratio of the ARF components (lateral to axial) for the single piezoelectric crystal simulation over the tested frequency range. FIG. 26 shows the normalized acoustic radiation force (ARF) from the 5-element simulation. FIG. 27 shows the ratio of the ARF components (lateral to axial) for the 5-element simulation over the tested frequency range. Comparing FIG. 24 to FIG. 26, the peak ARF for the 1-element simulation is about 6e-11, while the peak ARF for the 5-element simulation is about 2e-9. Comparing FIG. 25 to FIG. 27, the ratio of the forces is also more consistent, with a variation of about 0.60 compared to about 0.40.

Generally, the 4-element and 5-element arrays produced high ratios, including some greater than 0.9. Some of the simulations also had acoustic radiation force amplitudes that were almost two orders of magnitude higher than those produced by the 1-element transducer (which served as the baseline).

Figure 28:
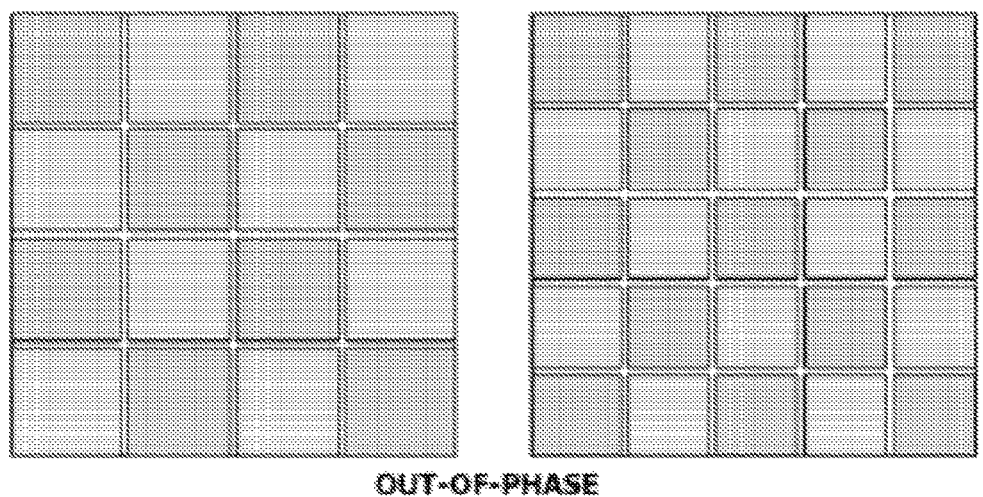
FIG. 28 is a diagram showing the phasing of the arrays during out-of-phase testing. Dark elements had a 0° phase angle and light element had a 180° phase angle when tested.

Experimental 16-element arrays and 25-element arrays were then tested. The feed solution was a 3% packed cell mass yeast solution, used as a simulant for CHO cells for biological applications. For out-of-phase testing, a checkerboard pattern of 0° and 180° phases was used. For the 25-element array, 12 elements were at 180° and 13 elements were at 0°. These checkerboard patterns are illustrated in FIG. 28. The left-hand side is the 16-element array and the right-hand side is the 25-element array, with the different shades indicating the different phase angle.

The turbidity of the feed, concentrate, and permeate were measured after 30 minutes at various frequencies. The concentrate was the portion exiting the device that contained the concentrated yeast, along with some fluid. The permeate was the filtered portion exiting the device, which was mostly liquid with a much lower concentration of yeast. A lower turbidity indicated a lower amount of yeast. The capture efficiency was determined as (feed-permeate)/feed*100%. The feed rate was 30 mL/min, and the concentrate flow rate was 5 mL/min. The power to the transducers was set at 8 W.

Table 4 lists results for the single-element transducer, which is used as a baseline or control.

TABLE 4

| | Frequency (MHz) | |
| --- | --- | --- |
| | 2.225 | 2.244 |
| Concentrate (NTU) | 15,400 | 15,400 |
| Permeate (NTU) | 262 | 327 |
| Feed (NTU) | 4,550 | 5,080 |
| Capture Efficiency (%) | 94.2 | 93.6 |

Table 5 lists results for the 16-element in-phase experiments.

TABLE 5

| Frequency (MHz) | 2.22 | 2.225 | 2.23 | 2.242 | 2.243 | 2.244 | 2.255 | 2.26 |
| --- | --- | --- | --- | --- | --- | --- | --- | --- |
| Concentrate (NTU) | 22,700 | 24,300 | 22,500 | 24,600 | 23,100 | 28,100 | 27,400 | 23,800 |
| Permeate (NTU) | 205 | 233 | 241 | 201 | 249 | 197 | 244 | 165 |
| Feed (NTU) | 5,080 | 4,850 | 5,100 | 4,830 | 4,810 | 5,080 | 4,940 | 4,830 |
| Capture Efficiency (%) | 96.0 | 95.2 | 95.3 | 95.8 | 94.8 | 96.1 | 95.1 | 96.6 |

Table 6 lists results for the 16-element out-of-phase experiments.

TABLE 6

| Frequency (MHz) | 2.22 | 2.225 | 2.23 | 2.242 | 2.243 | 2.244 | 2.255 | 2.26 |
| --- | --- | --- | --- | --- | --- | --- | --- | --- |
| Concentrate (NTU) | 40,900 | 21,400 | 26,000 | 49,300 | 19,100 | 55,800 | 22,100 | 35,000 |
| Permeate (NTU) | 351 | 369 | 382 | 1,690 | 829 | 761 | 397 | 581 |
| Feed (NTU) | 5,590 | 4,870 | 5,860 | 5,160 | 5,040 | 4,870 | 4,800 | 5,170 |
| Capture Efficiency (%) | 93.7 | 92.4 | 93.5 | 67.2 | 83.6 | 84.4 | 91.7 | 88.8 |

Comparing the 16-element array results to each other and the control, the in-phase array maintains high capture efficiency through the frequency range, while the out-of-phase array drops off quickly around 2.24 MHz. The efficiency results are very similar to the control for most in-phase tests. The in-phase efficiency was higher than the out-of-phase efficiency at every frequency.

Table 7 lists results for the 25-element in-phase experiments.

TABLE 7

| Frequency (MHz) | 2.2190 | 2.2300 | 2.2355 | 2.2470 | 2.2475 | 2.2480 | 2.2485 | 2.2615 |
|---|---|---|---|---|---|---|---|---|
| Concentrate (NTU) | 13,300 | 19,800 | 20,900 | 21,400 | 13,700 | 17,300 | 19,000 | 19,500 |
| Permeate (NTU) | 950 | 669 | 283 | 1,044 | 1,094 | 1,164 | 688 | 797 |
| Feed (NTU) | 4,930 | 4,930 | 4,910 | 5,010 | 4,950 | 5,220 | 5,010 | 5,110 |
| Capture Efficiency (%) | 80.7 | 86.4 | 94.2 | 79.2 | 77.9 | 77.7 | 86.3 | 84.4 |

Table 8 lists results for the 25-element out-of-phase experiments.

TABLE 8

| Frequency (MHz) | 2.2190 | 2.2300 | 2.2355 | 2.2470 | 2.2475 | 2.2480 | 2.2485 | 2.2615 |
|---|---|---|---|---|---|---|---|---|
| Concentrate (NTU) | 14,605 | — | 21,700 | 18,025 | 23,425 | 22,575 | 21,900 | 22,450 |
| Permeate (NTU) | 2,568 | 2,541 | 1,484 | 1,134 | 1,005 | 987 | 905 | 2,034 |
| Feed (NTU) | 5,610 | 6,020 | 5,200 | 6,010 | 5,880 | 5,840 | 5,860 | 5,880 |
| Capture Efficiency (%) | 54.2 | 57.8 | 71.5 | 81.1 | 82.9 | 83.1 | 84.6 | 65.4 |

Comparing the 25-element array results to each other and the control, both arrays are less efficient than the control. The 25-element in-phase array peaks around 95% and then drops off in both directions. The out-of-phase array peaks around 85% efficiency and drops off sharply. The efficiency results are very similar to the control. It should be noted that the high peak amplitudes found using the numerical model have not been tested experimentally.

Figure 29:
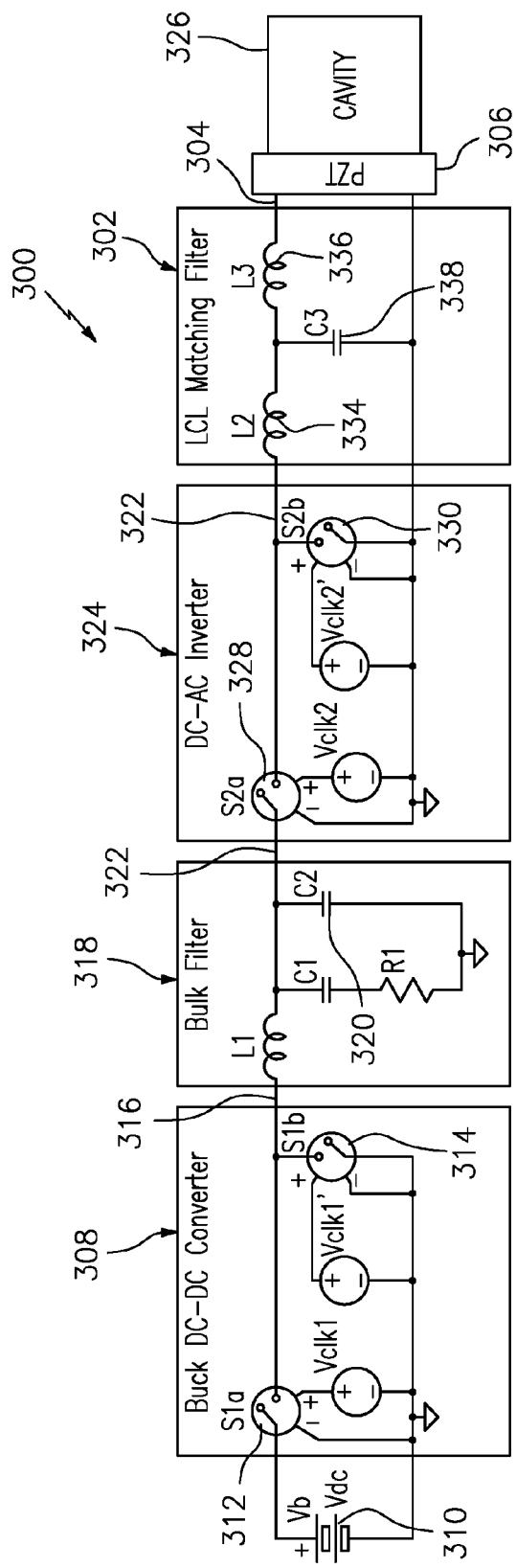
FIG. 29 is a circuit diagram of an RF power supply with an LCL network that provides a transducer drive signal to an ultrasonic transducer.

FIG. 29 is a circuit diagram of an RF power supply 300 with an LCL filter network 302 that provides a transducer drive signal on a line 304 to an ultrasonic transducer 306. In this embodiment, a DC-DC converter 308 receives a first DC voltage from a source 310 and switches 312, 314 (e.g., power MOSFETs) are cooperatively switched under the control of a controller (not shown) to generate a pulse width modulated (PWM) signal that is provided on a line 316. The switches 312, 314 are driven by first complementary clocking signals generated by the controller, and have the same frequency and duty cycle. The switches may not be closed at the same time, and the switching action produces a chopped voltage $V_b$ across the switch 314. The resultant PWM signal on the line 316 is received by a filter 318 (e.g., a buck filter) that filters the signal on the line 318 so the average voltage appears across capacitor $C_2$ 320, and is provided on line 322 to a DC-AC inverter 324. The bandwidth of the filter 318 is selected so the voltage on the line 322 follows changes in the duty cycle of the clocking signals that drive the switches 312, 314 based upon dynamic changes in acoustic cavity 326. Second complementary clocking signals generated by the controller drive switches 328, 330 to perform the DC to AC inversion, and a resultant AC signal is provided on line 332. The AC signal is then input to the matching filter network 302 (e.g., an LC, LCL, et cetera) which filters the input to attenuate higher frequency components of the input and provide a periodic signal such a sine wave on the line 304 to drive the transducer 306. In this embodiment, the LCL filter 302 includes serially connected inductors L2, L2, 334, 336 respectively and a capacitor C3 338 that extends from a node between the inductors 334, 336 to ground. LCL circuit 302 filters the output of the inverter 324 and matches the transducer 306 to the inverter 324 for improved power transfer.

The matching filter 302 provides impedance scaling to obtain an appropriate load for the inverter drive. The matching filter can be considered a network, which is tuned to provide desired power transfer, such as optimized power transfer, through the transducer 306 and into the resonant cavity 326. Considerations for implementing the filter 302 (e.g., LC or LCL) include the combined response of the transducer 306 and the resonant cavity 326. According to one example, the filter permits desired power transfer, such as optimized power transfer, when the acoustic transducer is operated in a multi-dimensional mode, or in a multimode, for example, with multiple overlaid vibrational modes that produce one or more primary or dominant vibrational modes. A desired mode of operation is at a frequency that corresponds to a low or minimum reactance point of the response of the transducer, and/or the response of the transducer/resonant cavity combination.

Figure 30:
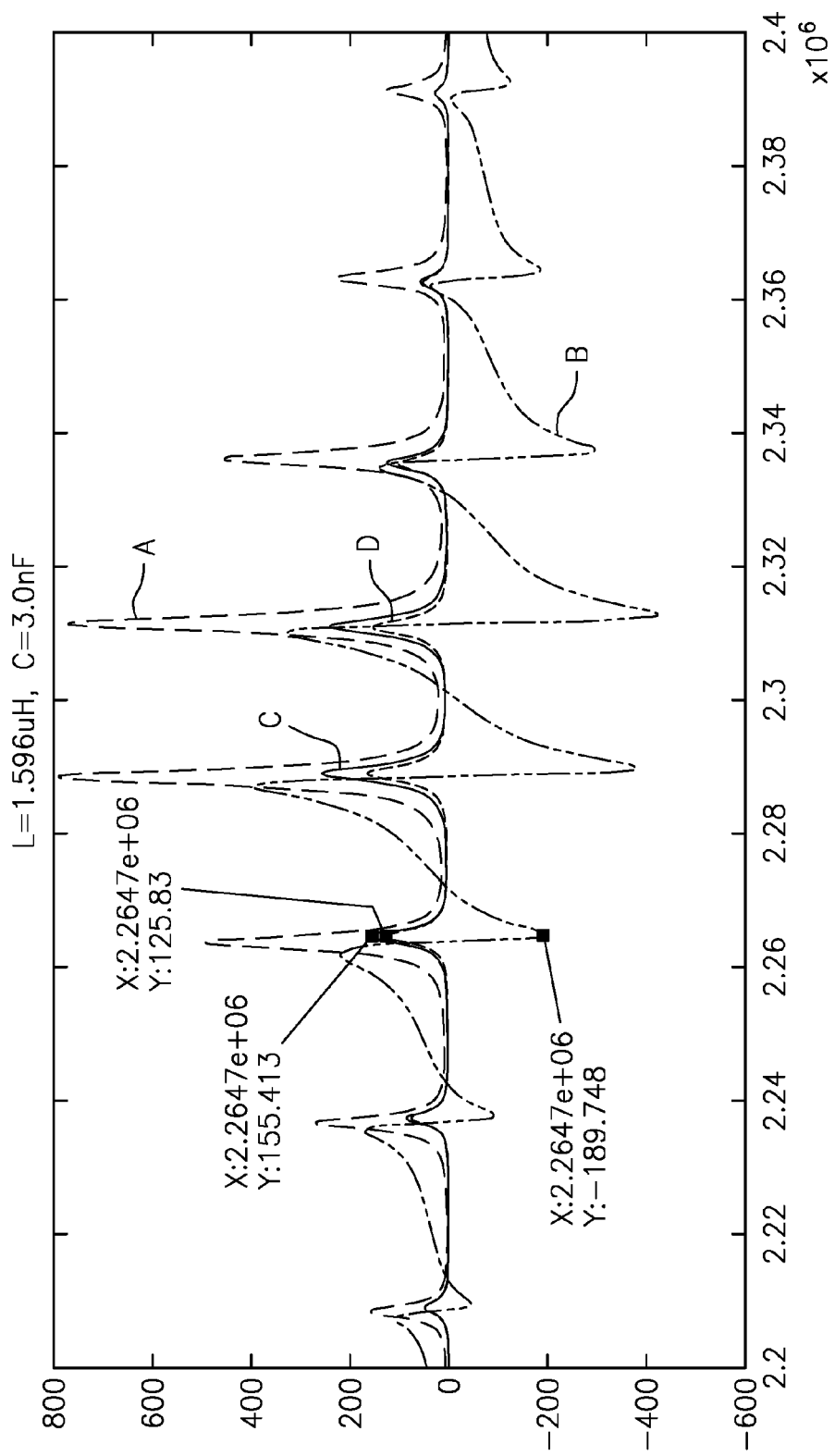
FIG. 30 is a graph illustrating a frequency response for an LC network.

For a fixed resonant frequency, the matching filter 302 may deliver different amounts of power based on the system resonance(s) in accordance with the combination of inductor and capacitor values that are used to form the matching filter network. FIG. 30 illustrates a response curve for matching filter configured as a LC network with an inductor value of 1.596 uH and a capacitor value of 3.0 nF. The resonant frequency of the LC network is 2.3 MHz. Referring to FIG. 30, the resistive impedance is labeled A, the reactive impedance is labeled B, the input real power is labelled C and the acoustic real power into the cavity is labelled D. With regard to the power delivered into the system, increasing the capacitor value with the same resonance increases power into the system. In general, changing the values of the inductor and/or capacitor can influence the resonant frequency of the LC network. Changing the resonant frequency of the LC network changes the frequency at which optimum power transfer occurs, and can impact the efficiency of the transfer. For example, the frequency for optimum power transfer relative to lower or minimum reactance points (label B) of the input impedance of the system is influenced by the resonance frequency of the LC network.

The plot in FIG. 30 shows the points on the input real power (C) and the acoustic real power (D) at a reactance minimum. The input real power and acoustic real power are fairly well matched, indicating efficient transfer of power. If the value of the inductor is changed to 0.8 uH and the value of the capacitor is changed to 6.0 nF, then the same reactance minimum produces a greater power transfer with somewhat less efficiency. The power transfer becomes less efficient when the input real power (C) is significantly different (greater) than the acoustic real power (D). In some instances, depending on the inductor and capacitor values, power transfer can be highly efficient, however, the frequency operating point may not be at a minimum reactance point (B). Accordingly, choices can be made between operating the transducer to obtain highly efficient separation in the acoustic chamber, implying a minimum reactance point, and obtaining efficient power transfer into the chamber. For a given material being separated and a given transducer, an LC network can be selected with a resonance frequency to obtain efficient power transfer into the acoustic cavity, improving overall system efficiency.

Figure 31:
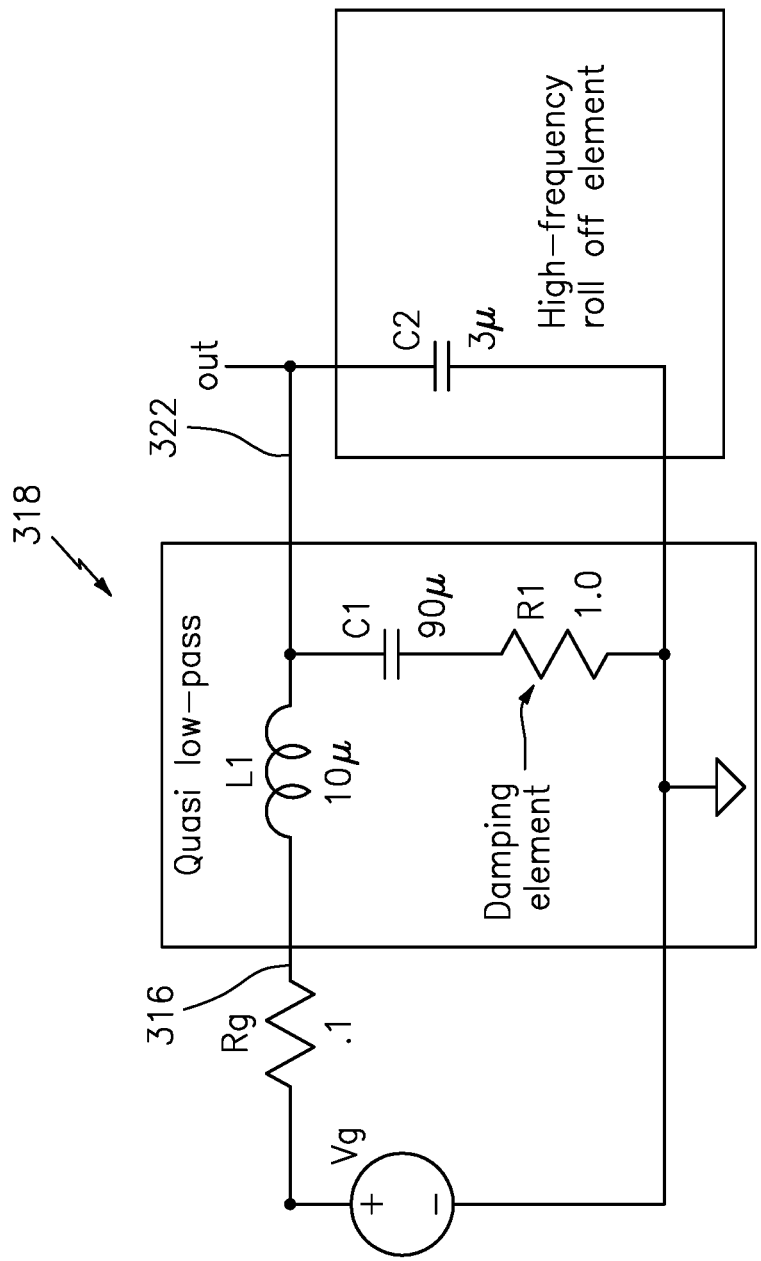
FIG. 31 is a circuit diagram of a buck low pass filter used with the RF power supply of FIG. 29.

FIG. 31 is a circuit diagram of one embodiment of the buck filter 318 illustrated in FIG. 29. The component values illustrated in FIG. 31 are presented by way of example, other values and component combinations may be used to provide the desired filtering.

Figure 32:
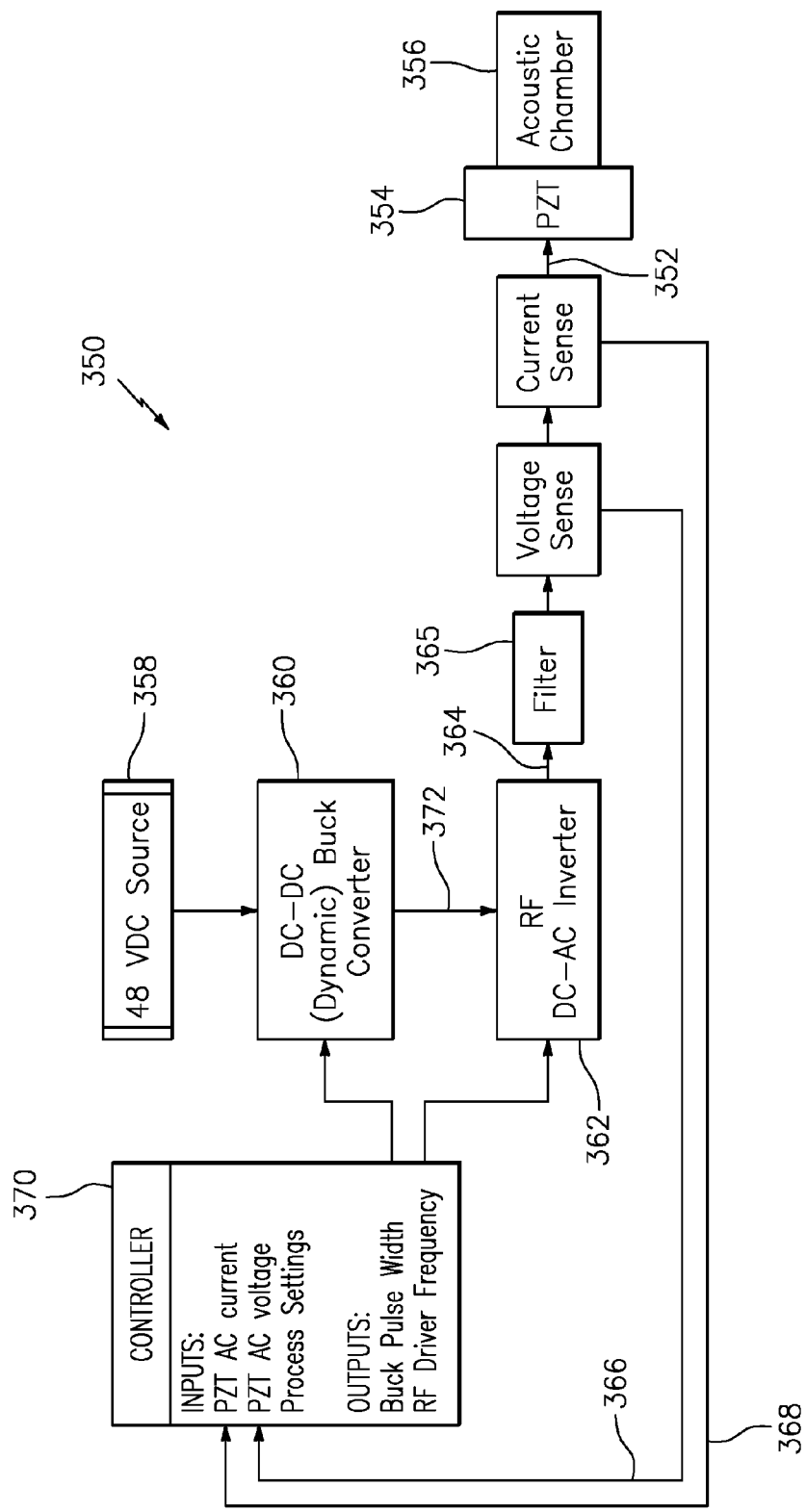
FIG. 32 is a block diagram illustration of a system for providing the transducer drive signal to the transducer.

FIG. 32 is a block diagram illustration of a system 350 for providing a transducer drive signal on the line 352 to an acoustic transducer 354. Referring to FIG. 32, the system 350 controls the transducer 354, which is coupled to an acoustic chamber 356. The acoustic transducer 354 is driven by an RF power converter composed of a DC source 358 (e.g., 48 volts DC), a DC-DC converter 360 (e.g., a buck converter) and a RF DC-AC inverter 362. Inverter output drive signal on line 364 is input to a low pass filter 365 (e.g., an LC or LCL matching low pass filter as shown in FIG. 29) and the resultant filtered signal on line 367 is sensed to obtain a voltage sense signal on line 366 and a current sense signal on line 368, which are fed back to controller 370. The controller 370 provides control signals to the converter 360 and the inverter 362 to control the drive signal on the line 364.

The signal provided by the controller 370 to the converter 360 is a pulse width measure, which determines the duty cycle of the switching signals in the converter 360. The duty cycle determines the DC level on converter output signal on line 372, which is applied to the inverter 362. For example, the greater the duty cycle, the higher the DC output on the line 372. The controller 370 provides control signals to the inverter 362 that determine the frequency of operation of the inverter. The control signals provided to the inverter 362 may be switching signals, for switching switches (e.g., FETs) in the inverter, an example of such switches being shown in FIG. 29. Alternately, or in addition, the controller 370 may provide a control signal to the inverter 362 that is used to indicate a desired switching frequency, and circuitry internal to the inverter interprets the control signal and switches the internal switches in accordance with the interpreted control signal.

The voltage sense signal on the line 366 and the current sense signal on the line 368 are provided to the controller 370 as feedback signals to control the drive signal on the line 364 provided to the acoustic transducer 354. The controller 370 performs operations and calculations on the feedback signals on the lines 366, 368, for example, to obtain a power measure, P=V*I, or to obtain a phase angle, θ=arctan (X/R).

Figure 33:
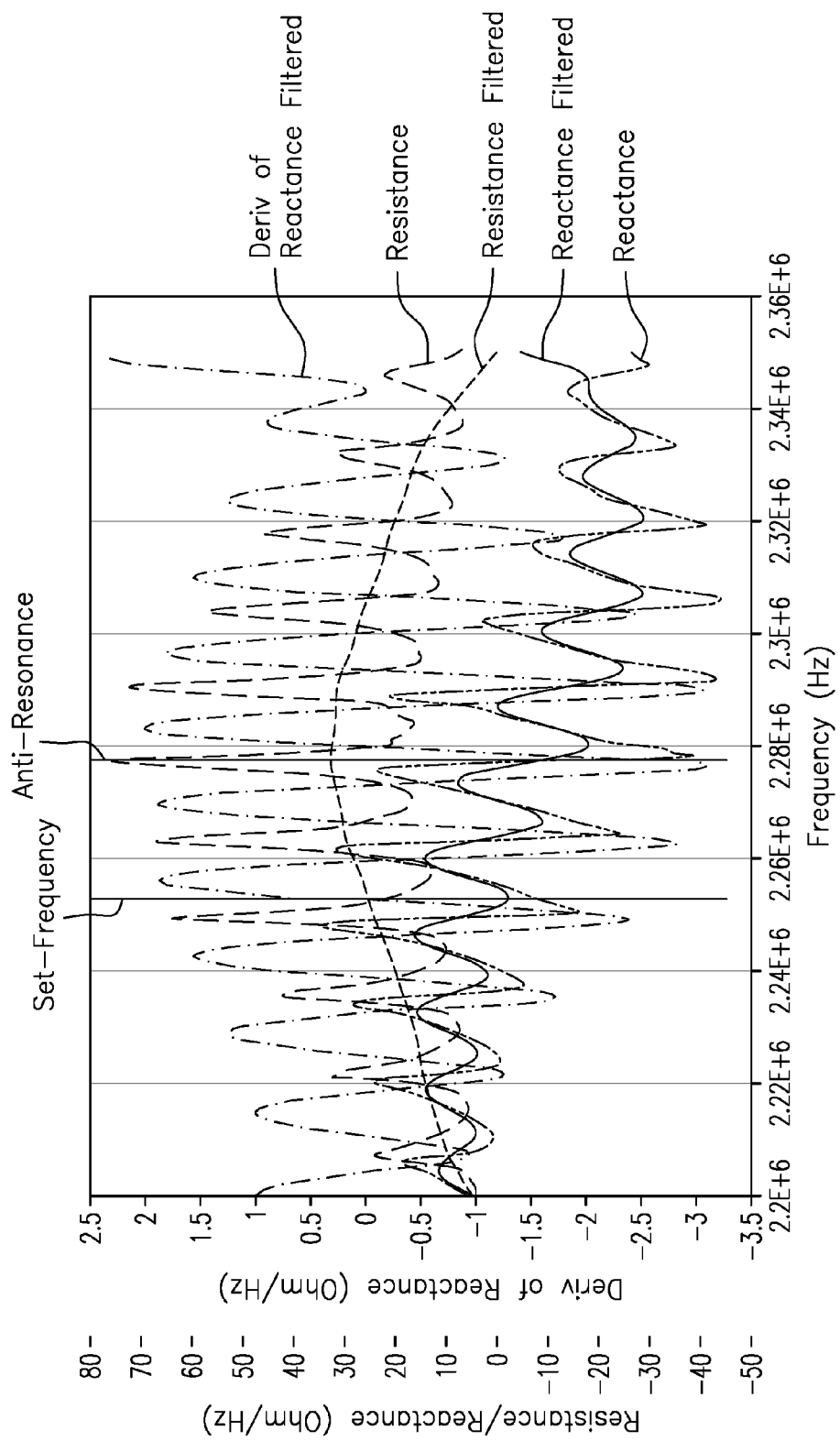
FIG. 33 is a graph illustrating a frequency response for an acoustic transducer.

The controller 370 is provisioned with a control scheme that accepts process settings, such as power output, range of frequency operation, or other user selectable parameters, and provides control signals to the converter 360 and the inverter 362 based on the process settings and the feedback values. For example, as described above, the controller can sequence through a number of frequencies in a range of frequencies that are provided to the inverter 362 to scan through the frequency range and determine the characteristics of the transducer 354 or the transducer 354 in combination with the acoustic chamber 356, which may be under load. The results of the frequency scan in terms of voltage and current obtained from the feedback signals on the lines 366, 368 are used to identify characteristics of the impedance curves for the components or the system, such as is illustrated in FIG. 33. FIG. 33 is a graph illustrating a frequency response for an acoustic transducer.

The frequency scan can be implemented to occur at set up, and/or at intervals during operation of the illustrated system. During steady-state operation, the frequency scan can be conducted to identify desired set points for operation, such as power or frequency, based on user settings and feedback values. The control scheme implemented by the controller 370 is thus dynamic, and responds to changing conditions in the system, such as may be encountered with frequency drift, temperature change, load changes and any other system parameter changes. The dynamic nature of the control scheme permits the controller to respond to or compensate for nonlinearities, such as may be encountered as components age or lose tolerance. Accordingly, the control scheme is adaptive and can accommodate system changes.

Referring still to FIG. 32, some examples of system operation include driving the acoustic transducer 354 to produce an acoustic standing wave (e.g., a multidimensional acoustic standing wave) in the acoustic chamber 356. For example, a 3D acoustic wave may be stimulated by driving the acoustic transducer 354, which may be implemented as a piezoelectric crystal, sometimes referred to herein as a PZT, near its anti-resonance frequency. Cavity resonances modulate the impedance profile of the PZT as well as affect its resonance modes. Under the influence of the 3D acoustic field, suspended particles in the liquid medium in the acoustic cavity 356 are forced into agglomerated sheets and then into strings of 'beads' of agglomerated material. Once particle concentrations reach a critical size, gravitational forces take over and the agglomerated material drops out of the acoustic field and to the bottom of the chamber. The changing concentrations of agglomerated material as well as the dropping out of that material affects the cavity's resonances which in turn change the acoustic loading on the PZT and its corresponding electrical impedance. The changing dynamics of the collected material detunes the cavity and PZT reducing the effects of the 3D wave in clarifying the medium. Additionally, changes in the medium and cavity temperature also detune the cavity so that clarification is reduced. To track the resonance changes occurring in the cavity, a control technique is used to follow changes in the PZT's electrical characteristics.

A strong 3D acoustic field can be generated by driving the PZT at a frequency where its input impedance is a complex (real and imaginary) quantity. However, cavity dynamics can cause that impedance value to change significantly in an erratic manner. The changes in impedance are due, at least in part, to changes in the load applied to the acoustic transducer 354 and/or the acoustic chamber 356. As particles or secondary fluid is separated from a primary or host fluid, the loading on the acoustic transducer and/or the acoustic chamber changes, which in turn can influence the impedance of the acoustic transducer and/or the acoustic chamber.

To correct for detuning, the controller 370 calculates the PZT impedance from the feedback signals on the lines 366, 368 to change the operating frequency to compensate for the detuning. Since frequency changes affect power delivered to the chamber 356, the controller 370 also determines how to adjust the output voltage of the (dynamic) converter 360 to maintain the desired amount of power output from the RF DC-AC inverter 362 and into the acoustic transducer 354 and/or the acoustic chamber 356.

The converter 360 (e.g., a buck converter) is an electronically adjustable DC-DC power supply and is the power source for the inverter 362. The inverter 362 converts the DC voltage on the line 372 to a high-frequency AC signal on the line 364, which is filtered by filter 365 to create a transducer drive signal that drives the PZT 354. The dynamics in the chamber 356 occur at rates corresponding to frequencies in the low audio band. Consequently, the converter 360, the controller 370, and the DC-AC inverter 362 are capable of working at rates faster than the low audio band to permit the controller to track chamber dynamics and keep the system in tune.

The controller 370 can simultaneously change the frequency of the DC-AC inverter 362 and the DC voltage coming out of the buck converter 360 to track cavity dynamics in real time. The control bandwidth of the system is a function of the RF bandwidth of the inverter and the cutoff frequency of the filtering system of the buck converter (e.g., see filter 318 in FIG. 29).

The controller 370 can be implemented as a DSP (digital signal processor) control, microcontroller, microcomputer, et cetera or as an application specific integrated circuit (ASIC) or a field programmable gate array (FPGA) control, as examples. The controller may be implemented with multiple channels, to permit parallel processing, for example to analyze real and/or reactive impedance, voltage, current and power.

The acoustic dynamics of the cavity 356 affects the electrical characteristics of the PZT 354, which affects the voltage and current drawn by the PZT. The sensed PZT voltage and current fed back on the lines 366, 368 is processed by the controller 370 to compute the real-time power consumed by the PZT as well as its instantaneous impedance (affected by acoustic dynamics). Based on user set points the controller 370 adjusts, in real-time, the DC power supplied on the line 372 to the inverter 362, and the frequency at which the inverter is operated to track cavity dynamics and maintain user set points. The filter 365 (e.g., an LC or LCL, et cetera) is used to impedance match the output impedance of the inverter 362 to increase power transfer efficiency.

The controller 370 samples the feedback signals on the lines 366, 368 fast enough to detect changes in cavity performance (e.g., via changes in PZT impedance) in real time. For example, the controller 370 may sample the feedback signals on the lines 366, 368 at one hundred million samples per second. Signal processing techniques are implemented to permit a wide dynamic range for system operation to accommodate wide variations in cavity dynamics and applications. The DC-DC converter 360 can be configured to have a fast response time to follow the signal commands coming from the controller 370. The inverter 362 can drive a wide range of loads that demand varying amounts of real and reactive power that change over time. The electronics package used to implement the system illustrated in FIG. 32 may be configured to meet or exceed UL and CE specifications for electromagnetic interference (EMI).

Figure 34:
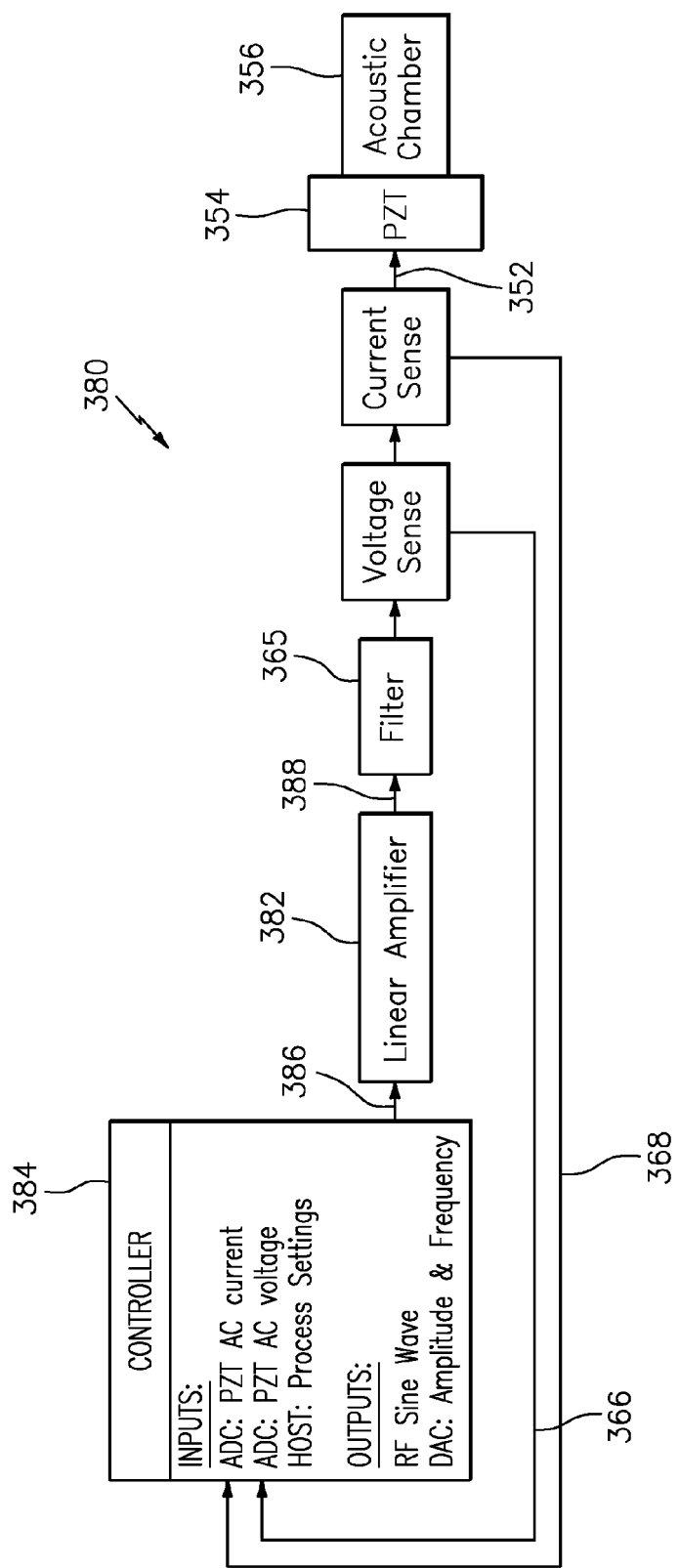
FIG. 34 is a block diagram illustration of an alternative embodiment system for providing the transducer drive signal to the transducer.
Figure 35:
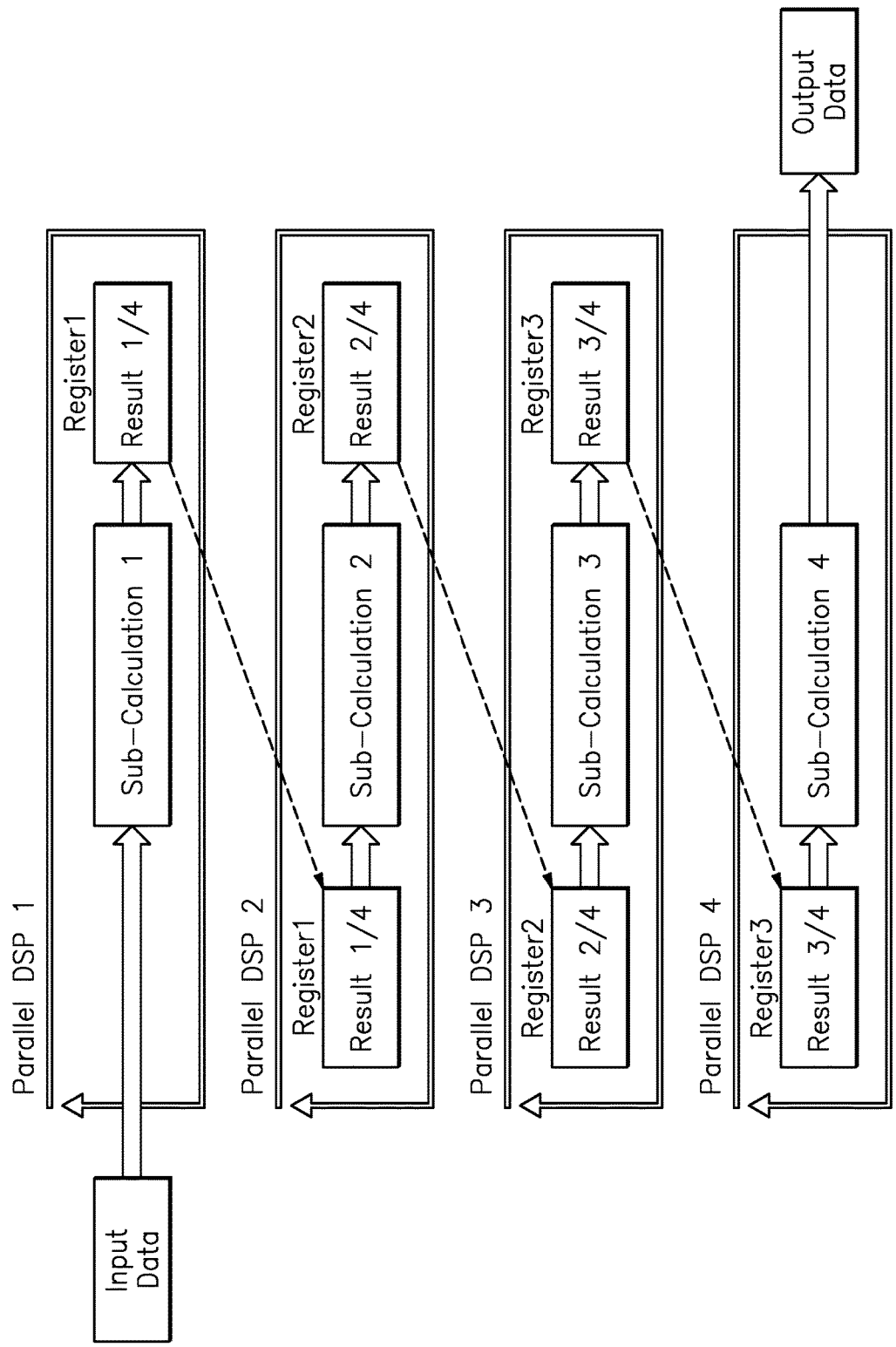
FIG. 35 is a block diagram illustrating a calculation technique for obtaining control parameters for an acoustic transducer.

FIG. 34 is a block diagram illustration of an alternative embodiment system 380 for providing the transducer drive signal 352 to the transducer 354. The embodiment of FIG. 34 is substantially the same as the embodiment in FIG. 32, with a primary difference that the DC-DC converter 360 and DC-AC inverter 362 of FIG. 32 have been replaced by a linear amplifier 382 (FIG. 32). In addition, the output of controller 384 would be an analog sine wave on line 386 that is input to the linear amplifier 382. Referring to FIG. 35, the controller 384 may be implemented with very-high-speed parallel digital-signal-processing loops using RTL (Register Transfer Level) which is realized in actual digital electronic circuits inside a field-programmable-gate-array (FPGA). Two high speed digital proportional integral (PI) loops adjust the frequency of the sine output signal on the line 386. The linear amplifier 382 amplifies the output signal on the line 386 and provides an amplified output signal on line 388, which is filtered using the low pass filter 365. The resultant voltage and current from the low pass filter 365 are fed back to the controller 384 on lines 366 and 368. Calculations may be performed in series by the controller 384 to generate control signals to linear amplifier 382. The linear amplifier may have a variable gain that is set by controller 384. The controller 384 (e.g., a FPGA) can be operated, for example, with a clocking signal of 100 MHz. In a real time system, the clock speed (e.g., sample rates, control loop update rates, et cetera) may be fast enough to properly monitor and adapt to conditions of the PZT 354 and/or the chamber 356. In addition, the structure of the FPGA permits each gate component to have a propagation delay commensurate with the clocking speed. The propagation delay for each gate component can be less than one cycle, or for example 10 ns with a clocking speed of 100 MHz.

Referring to FIG. 35, a diagram illustrates parallel and sequential operations for calculating control signals. The controller 384 may be configured to calculate the following parameters.

$$VRMS = \text{sqrt}(V1^2 + V2^2 + \ldots + Vn^2)$$

$$IRMS = \text{sqrt}(I1^2 + I2^2 + \ldots + In^2)$$

Real Power($P = V$-Inst.$\times I$-Inst Integrated over $N$ Cycles)

Apparent Power($S = VRMS \times IRMS$)

Figure 36:
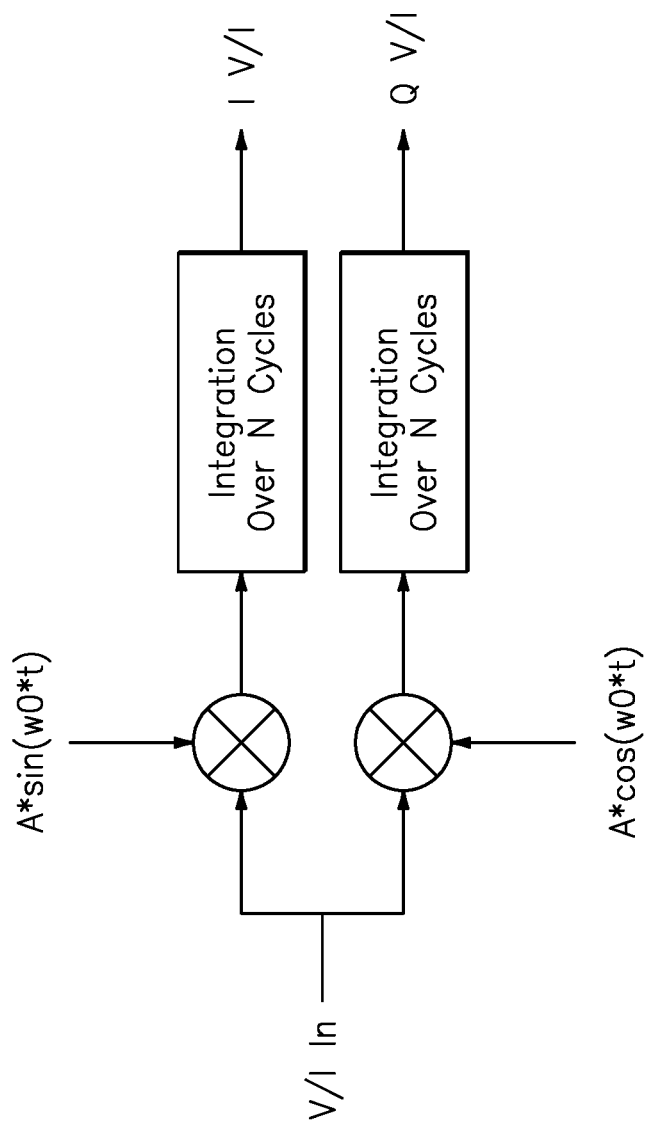
FIG. 36 is a block diagram illustrating demodulation of a voltage or current signal.

The controller 384 may be configured to calculate reactive power and bipolar phase angle by decomposing sensed voltage and current into in-phase and quadrature-phase components. FIG. 36 illustrates the in-phase and quadrature-phase demodulation of the voltage and current to obtain a four-quadrant phase, reactive power and reactance. The calculations for reactive power and phase angle can be simplified using the in-phase and quadrature-phase components.

$V$Pase Angle = Arctan($QV/IV$)

$I$Phase Angle = Arctan($QI/II$)

Phase Angle = $V$Phase − $I$Phase

Reactive Power = ($Q$ = Apparent Power × Since(Phase Angle)

The controller 384 may implement a control scheme that begins with a frequency sweep to determine system performance parameters at discrete frequencies within the frequency sweep range. The control scheme may accept inputs of a start frequency, a frequency step size and number of steps, which defines the frequency sweep range. The controller provides control signals to the linear amplifier 382 to modulate the frequency applied to the PZT 354, and the voltage and current of the PZT are fed back to the controller on lines 366, 368. The control scheme of the controller 384 may repeat the frequency sweep a number of times to determine the system characteristics, for example, reactance, with a relatively high level of assurance.

A number of reactance minimums can be identified as a result of analysis of the data obtained in the frequency sweep. The control technique can be provided with an input that specifies a certain frequency range where a desired reactance minimum is located, as well as being provided with a resistance slope (+/−) that can be used for tracking a desired point of operation based on resistance tracking that corresponds to a desired minimum reactance. The resistance slope may be constant near the minimum reactance, which may provide a useful parameter for use with a tracking technique. By tracking resistance at a desired frequency, a robust control can be attained for operating at a minimum reactance point.

The control technique may take the derivative of the resistance/reactance values to locate zero slope derivatives, which are indicative of maximums and minimums. A proportional-integral-differential (PID) controller loop may be used to track the resistance to obtain a frequency setpoint at which a desired minimum reactance occurs. In some implementations, the control may be a proportional-integral (PI) loop. With the FPGA operating at 100 MHz, adjustments or frequency corrections can be made every 10 ns to compensate for changes in the tracked resistance. This type of control can be very accurate and implemented in real-time to manage control of the PZT in the presence of a number of changing variables, including reactance, load and temperature, for examples. The control technique can be provided with an error limit for the frequency of the reactance minimum or frequency setpoint, to permit the control to adjust the output to linear amplifier 382 to maintain the frequency within the error limit.

A fluid mixture, such as a mixture of fluid and particulates, may be flowed through the acoustic chamber to be separated. The fluid mixture flow may be provided via a fluid pump, which may impose perturbations on the fluid, as well as the PZT and chamber. The perturbations can create a significant fluctuation in sensed voltage and current amplitudes, indicating that the effective impedance of the chamber fluctuates with pump perturbations. However, owing to the speed of the control technique, the fluctuations can be almost completely canceled out by the control method. For example, the perturbations can be identified in the feedback data from the PZT and can be compensated for in the control output from the controller. The feedback data, for example the sensed voltage and current, may be used to track the overall acoustic chamber pressure. As the characteristics of the transducer and/or acoustic chamber change over time and with various environmental parameters, such as pressure or temperature, the changes can be sensed and the control technique can compensate for the changes to continue to operate the transducer and acoustic chamber at a desired setpoint. Thus, a desired setpoint for operation can be maintained with very high accuracy and precision, which can lead to optimized efficiency for operation of the system.

The FPGA may be implemented as a standalone module and may be coupled with a class-D driver. Each module may be provided with a hardcoded address so that it can be identified when connected to a system. The module can be configured to be hot-swappable, so that continuous operation of the system is permitted. The module may be calibrated to a particular system and a transducer, or may be configured to perform a calibration at particular points, such as upon initialization. The module may include long-term memory, such as an EEPROM, to permit storage of time in operation, health, error logs and other information associated with operation of the module. The module is configured to accept updates, so that new control techniques can be implemented with the same equipment, for example.

Figure 37:
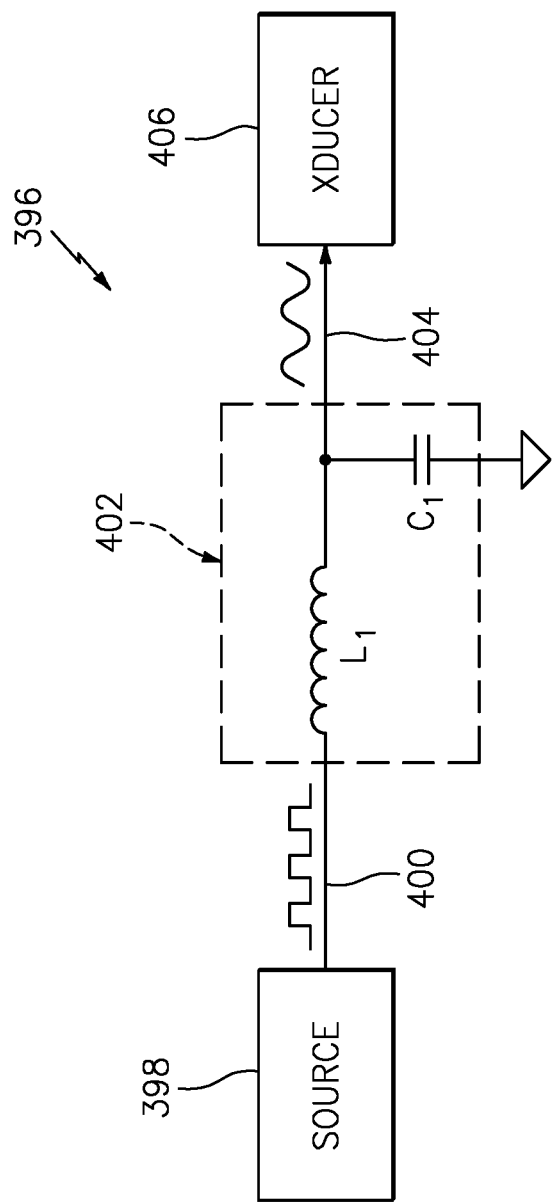
FIG. 37 is a simplified illustration of an RF power supply including an LC filter that provides the transducer drive signal.
Figure 38:
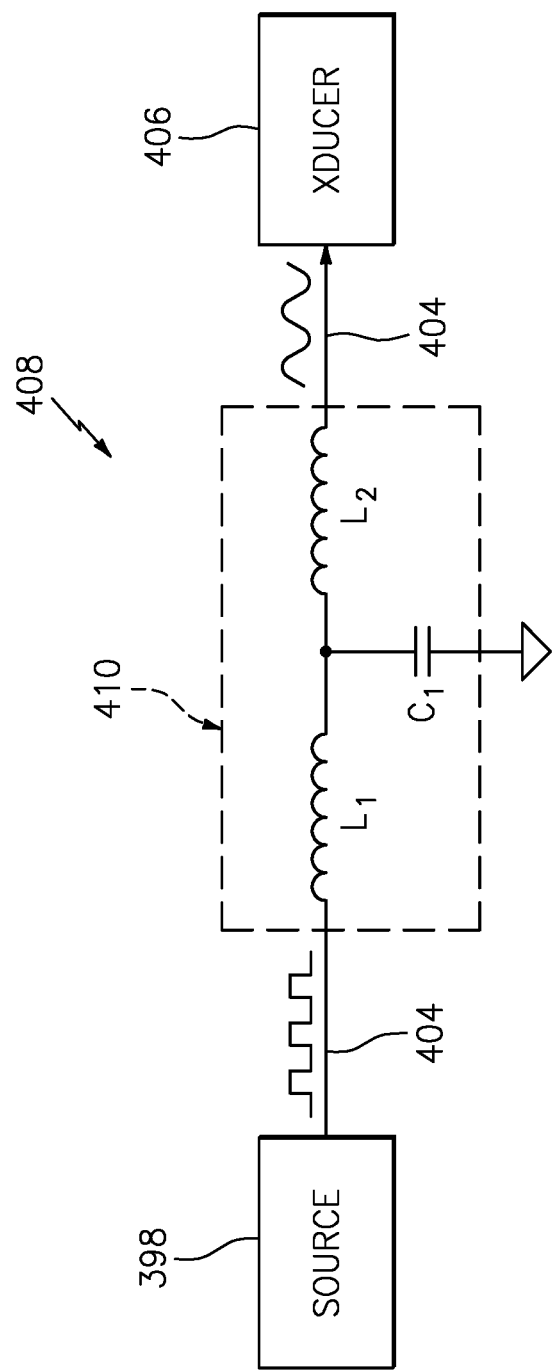
FIG. 38 is a simplified illustration of an alternative RF power supply including an LCL filter that provides the transducer drive signal.

FIG. 37 is a simplified circuit illustration of an RF power supply 396 that includes a voltage source 398 what provides a signal on a line 400 to an LC matching filter 402, which provides a transducer drive signal on line 404 to ultrasonic transducer 406. FIG. 38 is a simplified circuit illustration of an RF power supply 408 substantially the same as the power supply illustrated in FIG. 36, with the exception of an LCL matching filter 410 rather than the LC filter 402 illustrated in FIG. 36.

Figure 39:
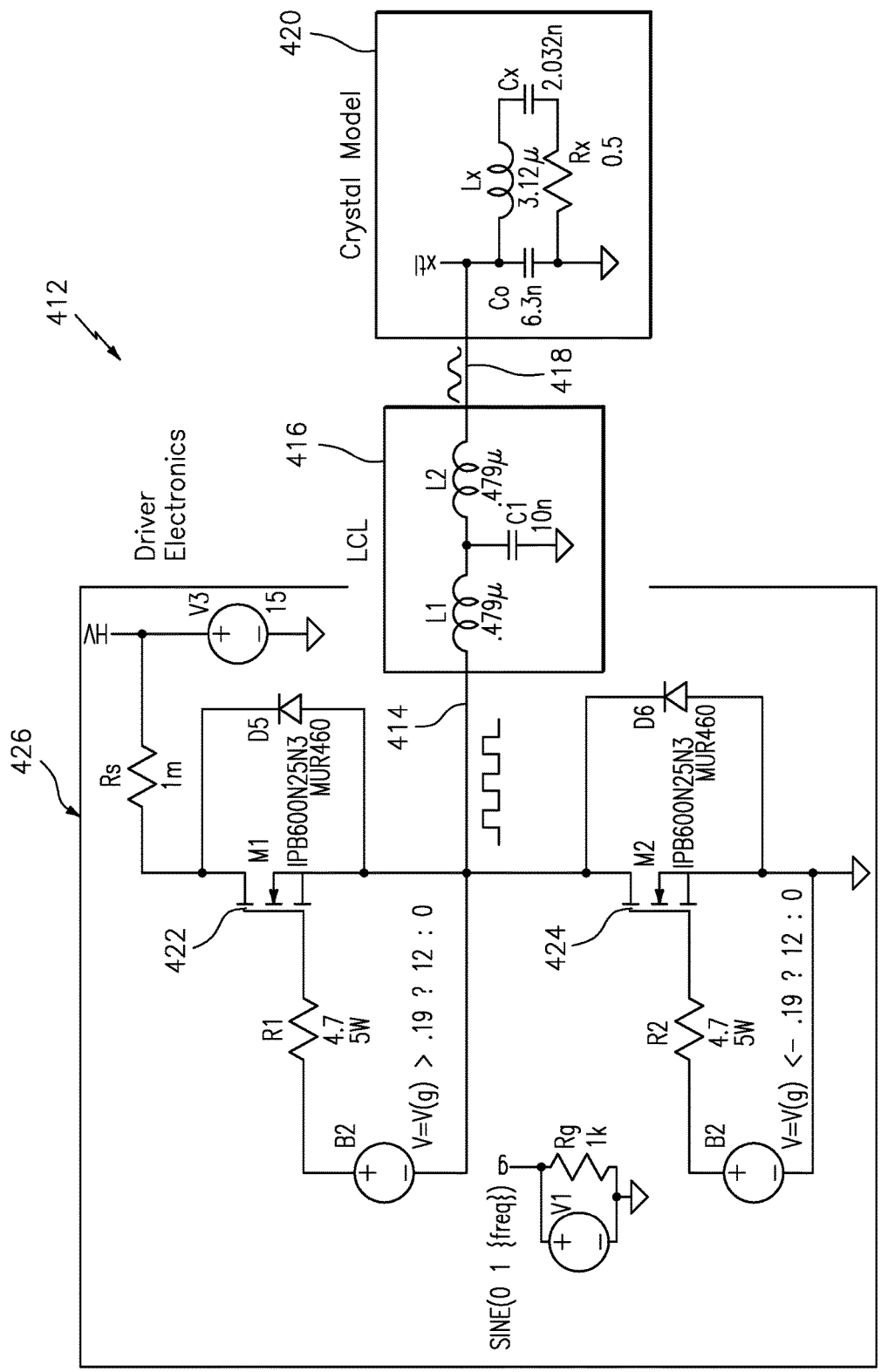
FIG. 39 is a circuit diagram of an RF power supply that provides a drive signal to an LCL filter that provides a transducer drive signal to an ultrasonic transducer.

FIG. 39 is a circuit diagram of an RF power supply 412 that provides a drive signal on line 414 to an LCL low pass filter 416, which provides a transducer drive signal on line 418 to an ultrasonic transducer 420. A controller (e.g., see controller 370 in FIG. 32) provides complementary control signals to first FET switch 422 and second FET switch 424 of a DC-AC inverter 426, and the resultant AC drive signal is provided on the line 414. The frequency of the complementary controls signals applied to the switches 422, 424 is controlled by the controller in order to set the frequency of the signal on the line 414. The signal on the line 414 is low pass filtered to attenuate high frequency components, and ideally provide a sine wave on line 418. An example of a dynamic model of the ultrasonic transducer 420 is also illustrated in FIG. 39.

Figure 40:
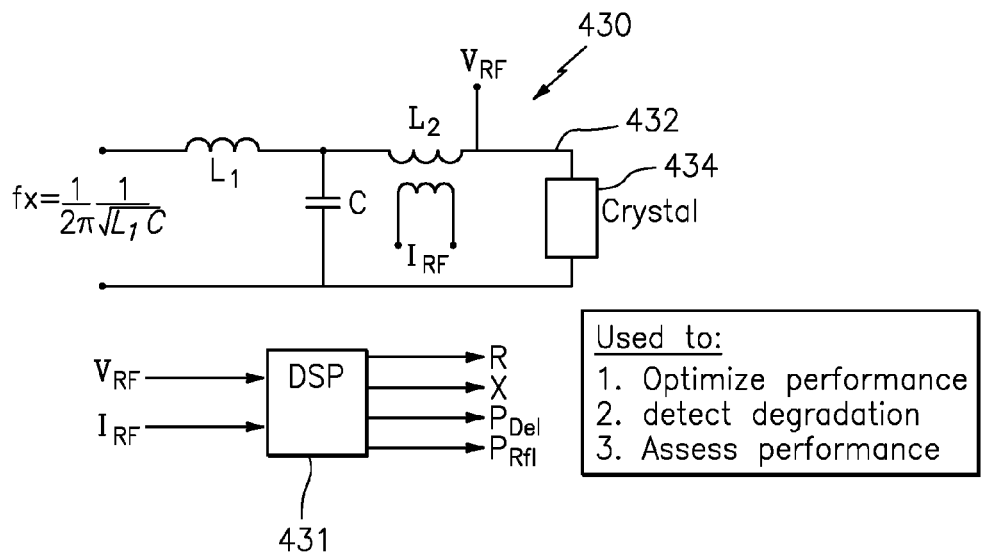
FIG. 40 is a circuit illustration of an LCL filter circuit with a tap that provides a current sense signal and a node that provides a voltage sense signal that can be fed back to a controller (e.g., a DSP) to control the drive signal delivered to the transducer.

FIG. 40 is a simplified circuit illustration of an LCL filter circuit 430 with a tap that provides a current sense signal $I_{RF}$ and a node that provides a voltage sense signal $V_{RF}$. The signals $I_{RF}$ and $V_{RF}$ are fed back to a controller 431 (e.g., a DSP) to control a transducer drive signal (e.g., frequency and power) on a line 432 applied to transducer 434.

Figure 41:
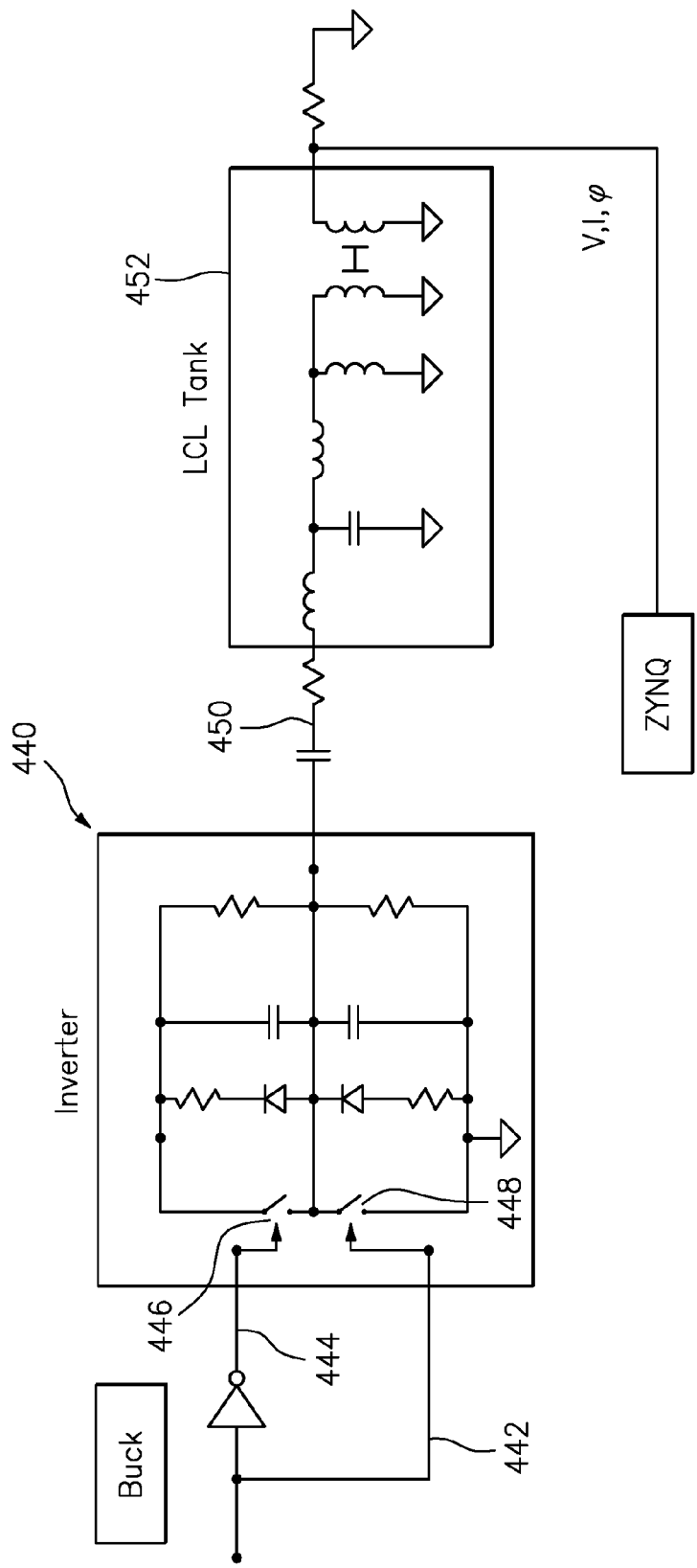
FIG. 41 is a schematic illustration of an embodiment of a power supply with an LCL filter network that provides a transducer drive signal.

FIG. 41 is a schematic illustration of an embodiment of a power supply that includes an inverter 440 that receives from a controller (not shown) a switching signal on line 442 and a complement thereof on line 444, which a used to drive first and second FETs 446, 448. The resultant AC signal on line 450 is input to a LCL filter 452, and the resultant filtered signal is output to drive the transducer. The filter 452 acts as a current source to drive the transducer.

It is contemplated that drivers and filters disclosed herein may be used to generate planar waves.

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

What is claimed is:

1. An apparatus for separating a second fluid or a particulate from a host fluid, comprising:
   a flow chamber with at least one inlet and at least one outlet;
   a control circuit configured to provide a drive signal;
   a scaling circuit that can receive the drive signal and provide an equivalent current source drive signal, where the scaling circuit provides impedance and source translation with respect to the ultrasonic transducer;
   an ultrasonic transducer, with a transducer input impedance, coupled to the flow chamber, the transducer includes at least one piezoelectric element configured to be driven by the equivalent current source drive signal to create an acoustic standing wave in the flow chamber; and
   at least one reflector opposite from the at least one ultrasonic transducer,
   where the acoustic standing wave comprises a multi-dimensional acoustic standing wave.

2. The apparatus of claim 1, where the control circuit comprises a voltage source.

3. The apparatus of claim 1, where the scaling circuit comprises an inductor that includes a first terminal and a second terminal, and a capacitor that includes a third terminal and a fourth terminal, where the first terminal receives the drive signal, the second and third terminals are connected, the fourth terminal is connected to a reference potential, and a signal indicative of the equivalent current source drive signal is provided at the second and third terminals.

4. The apparatus of claim 1, wherein the scaling circuit consists of passive circuit components.

5. An apparatus for separating a secondary fluid or particulates from a host fluid, comprising:
- a flow chamber with at least one inlet and at least one outlet;
- a circuit configured to receive a voltage drive signal and provide a translated drive signal;
- an ultrasonic transducer, coupled to the flow chamber, the transducer including at least one piezoelectric element that can receive the translated drive signal to create an acoustic standing wave in the flow chamber; and
- at least one reflector opposite from the at least one ultrasonic transducer,
- where the acoustic standing wave includes a multi-dimensional acoustic standing wave.

6. The apparatus of claim 5, further comprising a first tap that senses voltage across the ultrasonic transducer, which includes a crystal, and provides a sensed voltage signal indicative thereof, and a current sensing coil that senses current and provides a sensed current signal indicative of crystal current.

7. The apparatus of claim 6, further comprising a controller that receives and processes the sensed current signal and the sensed voltage signal to control the drive signal.

8. The apparatus of claim 6, where the circuit comprises a first inductor that includes a first terminal and a second terminal, a first capacitor that includes a third terminal and a fourth terminal, and a second inductor that includes a fifth terminal and sixth terminal, there the first terminal receives a signal indicative of the drive signal, the second terminal is connected to the third terminal and the fifth terminal, the fourth terminal is connected to a reference voltage, and an output signal indicative of the current drive signal is provided on the sixth terminal.

9. An apparatus for separating a secondary fluid or particulates from a host fluid, comprising:
- a flow chamber with at least one inlet and at least one outlet;
- a circuit configured to receive a voltage drive signal and provide a translated drive signal;
- an ultrasonic transducer, coupled to the flow chamber, the transducer including at least one piezoelectric element that can receive the translated drive signal to create an acoustic standing wave in the flow chamber; and
- at least one reflector opposite from the at least one ultrasonic transducer,
- where the circuit comprises a scaling circuit that receives the drive signal and provides the translated drive signal, where the scaling circuit provides impedance and source translation with respect to the ultrasonic transducer.

10. The apparatus of claim 9, where the scaling circuit comprises a first inductor, a first capacitor and a second inductor cooperatively arranged as a low pass filter.

11. The apparatus of claim 9, where the scaling circuit comprises an inductor that includes a first terminal and a second terminal, and a capacitor that includes a third terminal and a fourth terminal, where the first terminal receives the drive signal, the second and third terminals are connected, the fourth terminal is connected to a reference potential, and a signal indicative of the equivalent translated drive signal is provided at the second and third terminals.

12. The apparatus of claim 9, wherein the scaling circuit consists of passive circuit components.

13. An apparatus for separating a second fluid or a particulate from a host fluid, comprising:
- a flow chamber with at least one inlet and at least one outlet;
- a drive circuit configured to provide a drive signal;
- a filter circuit configured to receive the drive signal and provide a translated drive signal;
- an ultrasonic transducer cooperatively arranged with the flow chamber, the transducer including at least one piezoelectric element configured to be driven by the current drive signal to create an acoustic standing wave in the flow chamber; and
- at least one reflector opposing the ultrasonic transducer to reflect acoustic energy,
- where the acoustic standing wave comprises a multi-dimensional acoustic standing wave.

14. The apparatus of claim 13, where the filter circuit comprises a first inductor that includes a first terminal and a second terminal, a first capacitor that includes a third terminal and a fourth terminal, and a second inductor that includes a fifth terminal and sixth terminal, there the first terminal receives a signal indicative of the drive signal, the second terminal is connected to the third terminal and the fifth terminal, the fourth terminal is connected to a reference voltage, and an output signal indicative of the current drive signal is provided on the sixth terminal.

15. An apparatus for separating a second fluid or a particulate from a host fluid, comprising:
- a flow chamber with at least one inlet and at least one outlet;
- a drive circuit configured to provide a drive signal;
- a filter circuit configured to receive the drive signal and provide a translated drive signal;
- an ultrasonic transducer cooperatively arranged with the flow chamber, the transducer including at least one piezoelectric element configured to be driven by the current drive signal to create an acoustic standing wave in the flow chamber; and
- at least one reflector opposing the ultrasonic transducer to reflect acoustic energy,
- where the filter circuit comprises an inductor that includes a first terminal and a second terminal, and a capacitor that includes a third terminal and a fourth terminal, where the first terminal receives the drive signal, the second and third terminals are connected, the fourth terminal is connected to a reference potential, and a signal indicative of the equivalent current source drive signal is provided at the second and third terminals.

16. An apparatus for separating a second fluid or a particulate from a host fluid, comprising:
- a flow chamber with at least one inlet and at least one outlet;
- a drive circuit configured to provide a drive signal;
- a filter circuit configured to receive the drive signal and provide a translated drive signal;
- an ultrasonic transducer cooperatively arranged with flow chamber, the transducer including at least one piezoelectric element configured to be driven by the current drive signal to create an acoustic standing wave in the flow chamber; and at least one reflector opposing the ultrasonic transducer to reflect acoustic energy, where the filter circuit consists of passive circuit components.

17. The apparatus of claim 16, where the drive signal is a substantially a square wave, and the translated signal is substantially a sine wave.

* * * * *

UNITED STATES PATENT AND TRADEMARK OFFICE
CERTIFICATE OF CORRECTION

| | | |
|---|---|---|
| PATENT NO. | : 9,950,282 B2 | Page 1 of 1 |
| APPLICATION NO. | : 15/495471 | |
| DATED | : April 24, 2018 | |
| INVENTOR(S) | : Lipkens et al. | |

It is certified that error appears in the above-identified patent and that said Letters Patent is hereby corrected as shown below:

Column 9
Line 25, please delete "the"

Column 10
Line 56, please delete "(MU)" and insert --(ARF)--

Column 30
Line 45, please delete "VPase" and insert --VPhase--

Signed and Sealed this
Twenty-ninth Day of May, 2018

Andrei Iancu
*Director of the United States Patent and Trademark Office*